(12) United States Patent
Oh et al.

(10) Patent No.: US 9,914,919 B2
(45) Date of Patent: Mar. 13, 2018

(54) ALDOLASE, ALDOLASE MUTANT, AND METHOD AND COMPOSITION FOR PRODUCING TAGATOSE BY USING SAME

(71) Applicant: Konkuk University Industrial Cooperation Corp., Gwangjin-gu, Seoul (KR)

(72) Inventors: Deok-Kun Oh, Gwacheon-si (KR); Seung-Hye Hong, Seoul (KR); Seon-Hwa Lee, Gunsan-si (KR)

(73) Assignee: SAMYANG CORPORATION, Seoul (KR)

( * ) Notice: Subject to any disclaimer, the term of this patent is extended or adjusted under 35 U.S.C. 154(b) by 0 days.

(21) Appl. No.: 14/908,469

(22) PCT Filed: Jul. 25, 2014

(86) PCT No.: PCT/KR2014/006850
§ 371 (c)(1),
(2) Date: Jan. 28, 2016

(87) PCT Pub. No.: WO2015/016544
PCT Pub. Date: Feb. 5, 2015

(65) Prior Publication Data
US 2016/0186162 A1 Jun. 30, 2016

(30) Foreign Application Priority Data

Jul. 29, 2013 (KR) .................. 10-2013-0089588
Jan. 7, 2014 (KR) .................. 10-2014-0001709
Jul. 23, 2014 (KR) .................. 10-2014-0093443

(51) Int. Cl.
*C12N 9/88* (2006.01)
*C12P 19/02* (2006.01)
*C12P 7/26* (2006.01)

(52) U.S. Cl.
CPC .................. *C12N 9/88* (2013.01); *C12P 7/26* (2013.01); *C12P 19/02* (2013.01); *C12Y 401/02013* (2013.01)

(58) Field of Classification Search
None
See application file for complete search history.

(56) References Cited

FOREIGN PATENT DOCUMENTS

| | | |
|---|---|---|
| KR | 10-2002-0051835 | 6/2002 |
| KR | 10-2004-0035683 | 4/2004 |
| KR | 10-2007-0069357 | 7/2007 |
| KR | 10-0779160 | 11/2007 |
| KR | 10-1480422 | 1/2015 |
| WO | 2006-058092 | 6/2006 |
| WO | 2009-096693 | 8/2009 |
| WO | 2015-016544 | 2/2015 |

OTHER PUBLICATIONS

S.M Zgiby et al. "Exploring Substrate Binding and Discrimination in Fructose 1,6-bisphosphate and Tagatose 1,6-bisphosphate Aldolases", Eur. J. Biochem. 267:1858-1868 (2000).*
D.J. Wichelecki et al. "Protein-guided Identification of Novel D-Altritol and Galactitol Catabolic Pathways in Agrobacterium tumefaciens C58", J. Biol. Chem. 290(48):28963-28976. (2015).*
Davies et al., Fructose 1-phosphate and the regulation of glucokinase activity in isolated hepatocytes, European Journal of Biochemistry, 1990, pp. 283-289, vol. 192.
PCT International Search Report, PCT/KR2014/006850, dated Nov. 5, 2014.
PCT International Written Opinion, PCT/KR2014/006850, dated Nov. 5, 2014.
B. Siebers et al., "Archaeal Fructose-1,6-bisphosphate Aldolases Constitute a New Family of Archaeal Type Class I Aldolase", The Journal of Biologial Chemistry, vol. 276, No. 31, pp. 28710-28718, Aug. 3, 2001.
D.R. Hall et al., "Structure of Tagatose-1,6-bisphosphate Aldolase: Insight into Chiral Discrimination, Mechanism, and Specificity of class II Aldolases", The Journal of Biological Chemistry, vol. 277, No. 24, pp. 22018-22024, Jun. 14, 2002.
A. Galkin et al., "Characterization, Kinetics, and Crystal Structures of Fructose-1,6-bisphosphate Aldolase from the Human Parasite, Giardia lamblia", The Journal of Biological Chemistry, vol. 282, No. 7, pp. 4859-4867, Feb. 16, 2007.
NCBI GenBank Accession No. WP 011226657 fructose-bisphosphate aldolase [*Streptococcus thermophiles*] available at http://www.ncbi.nlm.nih.gov/protein/WP_011226657.1, dated Jan. 27, 2016.
NCBI GenBank Accession No. WP 011916728.1 fructose-bisphosphate aldolase, class II [Caldicellulosiruptor saccharolyticus] available at http://www.ncbi.nlm.nih.gov/protein/500265844, dated Jan. 27, 2016.
NCBI GenBank Accession No. XP 454290.1 hypothetical protein [Kluyveromyces lactis NRRL Y-1140] available at https://www.ncbi.nlm.nih.gov/protein/50308575, dated Jan. 27, 2016.
NCBI GenBank Accession No. WP 001521245 class II fructose-bisphosphate aldolase [*Escherichia coli*] available at http://www.ncbi.nlm.nih.gov/protein/WP_001521245.1, dated Jan. 27, 2016.
NCBI GenBank Accession No. WP 000034377.1 Multispecies: class II fructose-bisphosphate aldolase [Enterobacteriaceae] available at http://www.ncbi.nlm.nih.gov/protein/WP_000034377.1, dated Jan. 27, 2016.

(Continued)

*Primary Examiner* — Rebecca E Prouty
(74) *Attorney, Agent, or Firm* — Lex IP Meister, PLLC

(57) ABSTRACT

This disclosure relates to aldolase, an aldolase mutant, and a method and a composition for producing tagatose by using the same. The feature of the disclosure is environment-friendly due to the use of an enzyme acquired from microorganisms, requires only a simple process of enzyme immobilization, uses a low-cost substrate in a substrate compared with a conventional method for producing tagatose and has a remarkably high yield, thereby greatly reducing production costs and maximizing production effects.

2 Claims, 15 Drawing Sheets

(56) References Cited

OTHER PUBLICATIONS

NCBI GenBank Accession No. WP 000034372.1 Multispecies: class II fructose-bisphosphate aldolase [Proteobacteria] available at http://www.ncbi.nlm.nih.gov/protein/WP_000034372 dated, Jan. 27, 2016.

* cited by examiner

CLUSTAL 2.1 multiple sequence alignment

```
C. saccharolyticus    ------------------MPLVTTKEMFKKAAEGKYAIGAFNVNNMEIIQGIVEAAKEEQAPLIL  47
Nostoc_SP.            ------------------MALVPLRLLLDHAAENGYGIPAFNVNNLEQIQAILKAAAETDSPVIL  47
S. thermophilus       ------------------MAIVSAEKFVQSARDNGVALGGFNTNNLEWTQAILRAAEEAKKAPVLI 47
E. coli_K12           -MSKIFDFVKPGVITGDDVQKVFQVAKENNFALPAVNCVGTDSINAVLETAAKVKAPVIV  59
K. lactis             MPAQDVLTRKTGVIVGDDVKALFDYAKEHKFAIPAINVTSSSTVVAALEAARDNKSPIIL  60
C. glutaticum         ------------MPIATPEVVNEMLDRAKEGGFAFPAINCTSSETINAALKGFAEAESDGII  50
                                              .    *  . . .*    .         . .!  ::

C. saccharolyticus    QVSAGARKYAK---------------HYVLVKLVEAALEDS-GDLPIALHLDHGE-----  86
Nostoc_SP.            QASRGARNYAG---------------ENFLRHLILAAYETY-PEIPIVMHQQHGN-----  86
S. thermophilus       QTSMGAAKVMGG--------------VKLCKALIEELVESMGITVPVAIHLDHG-----  87
E. coli_K12           QFSNGGASFIAGKGVKSDVPQGAAILGAISGAHHVHQMAEHY--GVPVILHTDHCAKKLL 117
K. lactis             QTSNGGAAYFAGKGVSNEG--QNASIRGSIAAAHVIRSIAPAY--GIPVVLHTDHCAKKLL 117
C. glutaticum         QFSTGGAEFGSGLAVKNKV--------KGAVALAAFAHEAAKSY--GINVALHTDHCQKEVL 102
                      * * *.  !                              :  :  !* **

C. saccharolyticus    --------DFEICKACIDGG------FTSVMIDG---------SRLPFEENIALTKKVVEYAHERG 129
Nostoc_SP.            --------APSTCVSAIKNN------FTSVMNDGGSLEADAKTPASFEYNVNVTREVVNYAHALG 136
S. thermophilus       --------HVDDALECIEVG------YTSIMFDG---------SHLPIEENLKLAKEVVEKAHAKG 130
E. coli_K12           P-WIDGLLDAGEKHFAATGKPLFSSHMIDL--------SEESLQENIEICSKYLERMSKIG 169
K. lactis             P-WFDGMLKADEEYFAKHGEPLFSSHMLDL--------SEETDEENIGLCVKYFTRMAKIH 169
C. glutaticum         DEYVRPLLAISQERVDRGELPLFQSHMWDG--------SAVPIDENLEIAQELLAKAKAAN 155
                              ,  ! * * *           ,  . :*!   :  ,.

C. saccharolyticus    VVVEAELGKLAGIEDN-YKVAE-----------HEAAFTDPDQAAEFVERT------GVDSL 173
Nostoc_SP.            VSVEGELGCLGSLETG-AGEAEDGHGFEGTLDHSQLLTDPDEAVNFVEAT------QVDAL 190
S. thermophilus       ISVEAEVGTIGGEEDGIVGRGE-----------LAPIEDAKAMVAT------GVDFL 170
E. coli_K12           MTLEIELGCTGGEEDGVDNSHMDAS-----------ALVTQPEDVDYAYTELSKISP-RFTI 219
K. lactis             QWLEMEIGITGGEEDGVNNEGTSND-----------KLYTTPETVFSVHEALSKISP-NFSI 219
C. glutaticum         IILEVEIGVVGGEEDGVEAKAGAN-----------LYTSPEDFEKTIDAIGTGEKGRVLL 204
                       *  *:*   ,, * ,                   *                   :
```

FIG. 2

CLUSTAL 2.1 multiple sequence alignment

```
C. saccharolyticus    AVAIGTSHGAVKFKGEPR----LDFERLQRIVEKLPK--------GFPIVLHGASSVLPEFVE 224
Nostoc_SP.            AVAIGTSHGAVKFTRKPTGEILAISRIEEIHRRLPN---------THLVMHGSSSYPEDLIA 243
S. thermophilus       AAGIGNIHGPVPENWEG----LDLDHLQKLTEAIPG---------FPIVLHGGS--------- 211
E. coli_K12           AASFGNVHGVVKPGNVVLTPTILRDSQEVVSKKHN--LPHNS-LNFVFHGGS--------- 268
K. lactis             ASAFGNVHGVVKIA-AALKPELLGTFQDVAAKQLNKKAEDKP-LYLVFHGGS--------- 269
C. glutaticum         AATFGNVHGVVKPGNVKLRPEVLLEGQQVARKKLGLADDALP-FDFVFHGGS--------- 255
                       *  :*, ** *                        :         :*:**,*

C. saccharolyticus    MCNKYGGNIPGAKGVPEDMLRKAAELGVRKINIDTDLRLAMTAAIRKHLAE---------- 275
Nostoc_SP.            LINEVGGAIPETVGVPVEEIQKGIKSGVRKVNIDTDNRLAITAAVREALAK---------- 294
S. thermophilus       ---------------GIPDQIQEAIKLGVAKVNWNTECQIAFANATRKFVAEYE------- 251
E. coli_K12           ---------------GSTAQEIKDSVSYGVVKMNIDTDTQWATWEGVLNYVKANEAYLQGQL 315
K. lactis             ---------------GSSTKDFHTAIDFGVVKVNLDTDCQFAYLSGIRDYVLNKKDYLMTPV 316
C. glutaticum         ---------------GSEKEKIEEALTYGVIKMNVDTDTQVAFTRPIVSHMFENVNGVLKID 302
                                      *  , :, ,  ** *:*:*! : *     , C. saccharolyticus    -----------HPDHFDPRQVLKDGREAIKEMVKHKLRNVLGCSGKAPEI--------- 314
Nostoc_SP.            -----------NPKEFDPRHFLKPSITYMQKVCAERY-VQFGTAGNASKIKQVSLETFAAKV 344
S. thermophilus       ---ANEAEYDKKKLFDPRKFLKPGFEAITEAVEERI-DVFGSANKA------------ 293
E. coli_K12           GNPKGEDQPNKKYVDPRVWLRAGQTSMIARLEKAFQELNAIDVL-------------- 359
K. lactis             GNPTGEDSPNKKYYDPRVWYREGEKTMSKRITQALEIFRTKGALE------------- 361
C. glutaticum         G------EVGNKKAYDPRSYMKKAEQSMSERIIESCQDLKSVGKTTSK---------- 344
                            :   :***  !!! ,   :      , C. saccharolyticus    ----LEEIKKNRG- 323
Nostoc_SP.            AKGELNAISKAAAK 358
S. thermophilus       --------------
E. coli_K12           --------------
K. lactis             --------------
C. glutaticum         --------------
```

FIG. 3

| S. thermophilus | | K. lactis | | C. saccharolyticus | |
|---|---|---|---|---|---|
| Metal | Relative Activity(%) | Metal | Relative Activity(%) | Metal | Relative Activity(%) |
| None | 100.0 | None | 100.0 | None | 100.0 |
| EDTA | 89.7 | EDTA | 112.8 | EDTA | 108.2 |
| $ZnCl_2$ | 124.6 | $ZnCl_2$ | 114.1 | $ZnCl_2$ | 39.5 |
| $ZnSO_4$ | 104.9 | $ZnSO_4$ | 106.9 | $ZnSO_4$ | 37.3 |
| $MgCl_2$ | 41.7 | $MgCl_2$ | 51.7 | $MgCl_2$ | 59.8 |
| $MgSO_4$ | 42.2 | $MgSO_4$ | 54.8 | $MgSO_4$ | 48.7 |

| Metal | Relative Activity(%) |
|---|---|
| None | 98.7 |
| EDTA | 96.1 |
| $MgCl_2$ | 93.6 |
| $MgSO_4$ | 100.0 |
| $ZnSO_4$ | 44.9 |
| $ZnCl_2$ | 40.9 |

| Enzyme Amount(U/ml) | Relative Activity(%) |
|---|---|
| 50 | 100 |
| 20 | 50 |
| 10 | 17 |

SEQUENCE LISTING

```
<160> NUMBER OF SEQ ID NOS: 22

<210> SEQ ID NO 1
<211> LENGTH: 359
<212> TYPE: PRT
<213> ORGANISM: Escherichia coli (strain K12)

<400> SEQUENCE: 1

Met Ser Lys Ile Phe Asp Phe Val Lys Pro Gly Val Ile Thr Gly Asp
 1               5                  10                  15

Asp Val Gln Lys Val Phe Gln Val Ala Lys Glu Asn Asn Phe Ala Leu
            20                  25                  30

Pro Ala Val Asn Cys Val Gly Thr Asp Ser Ile Asn Ala Val Leu Glu
        35                  40                  45

Thr Ala Ala Lys Val Lys Ala Pro Val Ile Val Gln Phe Ser Asn Gly
    50                  55                  60

Gly Ala Ser Phe Ile Ala Gly Lys Gly Val Lys Ser Asp Val Pro Gln
65                  70                  75                  80
```

Gly Ala Ala Ile Leu Gly Ala Ile Ser Gly Ala His Val His Gln
                85                  90                  95

Met Ala Glu His Tyr Gly Val Pro Val Ile Leu His Thr Asp His Cys
        100                 105                 110

Ala Lys Lys Leu Leu Pro Trp Ile Asp Gly Leu Leu Asp Ala Gly Glu
    115                 120                 125

Lys His Phe Ala Ala Thr Gly Lys Pro Leu Phe Ser Ser His Met Ile
130                 135                 140

Asp Leu Ser Glu Glu Ser Leu Gln Glu Asn Ile Glu Ile Cys Ser Lys
145                 150                 155                 160

Tyr Leu Glu Arg Met Ser Lys Ile Gly Met Thr Leu Glu Ile Glu Leu
                165                 170                 175

Gly Cys Thr Gly Gly Glu Glu Asp Gly Val Asp Asn Ser His Met Asp
            180                 185                 190

Ala Ser Ala Leu Tyr Thr Gln Pro Glu Asp Val Asp Tyr Ala Tyr Thr
        195                 200                 205

Glu Leu Ser Lys Ile Ser Pro Arg Phe Thr Ile Ala Ala Ser Phe Gly
    210                 215                 220

Asn Val His Gly Val Tyr Lys Pro Gly Asn Val Val Leu Thr Pro Thr
225                 230                 235                 240

Ile Leu Arg Asp Ser Gln Glu Tyr Val Ser Lys His Asn Leu Pro
                245                 250                 255

His Asn Ser Leu Asn Phe Val Phe His Gly Ser Gly Ser Thr Ala
            260                 265                 270

Gln Glu Ile Lys Asp Ser Val Ser Tyr Gly Val Lys Met Asn Ile
        275                 280                 285

Asp Thr Asp Thr Gln Trp Ala Thr Trp Glu Gly Val Leu Asn Tyr Tyr
    290                 295                 300

Lys Ala Asn Glu Ala Tyr Leu Gln Gly Gln Leu Gly Asn Pro Lys Gly
305                 310                 315                 320

Glu Asp Gln Pro Asn Lys Lys Tyr Tyr Asp Pro Arg Val Trp Leu Arg
                325                 330                 335

Ala Gly Gln Thr Ser Met Ile Ala Arg Leu Glu Lys Ala Phe Gln Glu
            340                 345                 350

Leu Asn Ala Ile Asp Val Leu
        355

<210> SEQ ID NO 2
<211> LENGTH: 293
<212> TYPE: PRT
<213> ORGANISM: Streptococcus thermophilus

<400> SEQUENCE: 2

Met Ala Ile Val Ser Ala Glu Lys Phe Val Gln Ser Ala Arg Asp Asn
 1               5                  10                  15

Gly Tyr Ala Leu Gly Gly Phe Asn Thr Asn Asn Leu Glu Trp Thr Gln
            20                  25                  30

Ala Ile Leu Arg Ala Ala Glu Ala Lys Lys Ala Pro Val Leu Ile Gln
        35                  40                  45

Thr Ser Met Gly Ala Ala Lys Tyr Met Gly Gly Tyr Lys Leu Cys Lys
    50                  55                  60

Ala Leu Ile Glu Glu Leu Val Glu Ser Met Gly Ile Thr Val Pro Val
65                  70                  75                  80

Ala Ile His Leu Asp His Gly Tyr Asp Asp Ala Leu Glu Cys Ile
                85                  90                  95

```
Glu Val Gly Tyr Thr Ser Ile Met Phe Asp Gly Ser His Leu Pro Ile
                100                 105                 110

Glu Glu Asn Leu Lys Leu Ala Lys Glu Val Val Glu Lys Ala His Ala
            115                 120                 125

Lys Gly Ile Ser Val Glu Ala Glu Val Gly Thr Ile Gly Gly Glu Glu
        130                 135                 140

Asp Gly Ile Val Gly Arg Gly Glu Leu Ala Pro Ile Glu Asp Ala Lys
145                 150                 155                 160

Ala Met Val Ala Thr Gly Val Asp Phe Leu Ala Gly Ile Gly Asn
                165                 170                 175

Ile His Gly Pro Tyr Pro Glu Asn Trp Glu Gly Leu Asp Leu Asp His
                180                 185                 190

Leu Gln Lys Leu Thr Glu Ala Ile Pro Gly Phe Pro Ile Val Leu His
            195                 200                 205

Gly Gly Ser Gly Ile Pro Asp Asp Gln Ile Gln Glu Ala Ile Lys Leu
        210                 215                 220

Gly Val Ala Lys Val Asn Val Asn Thr Glu Cys Gln Ile Ala Phe Ala
225                 230                 235                 240

Asn Ala Thr Arg Lys Phe Val Ala Glu Tyr Glu Ala Asn Glu Ala Glu
                245                 250                 255

Tyr Asp Lys Lys Lys Leu Phe Asp Pro Arg Lys Phe Leu Lys Pro Gly
            260                 265                 270

Phe Glu Ala Ile Thr Glu Ala Val Glu Glu Arg Ile Asp Val Phe Gly
        275                 280                 285

Ser Ala Asn Lys Ala
        290

<210> SEQ ID NO 3
<211> LENGTH: 323
<212> TYPE: PRT
<213> ORGANISM: Caldicellulosiruptor saccharolyticus (strain ATCC
      43494 / DSM 8903)

<400> SEQUENCE: 3

Met Pro Leu Val Thr Thr Lys Glu Met Phe Lys Ala Ala Glu Gly
  1               5                  10                  15

Lys Tyr Ala Ile Gly Ala Phe Asn Val Asn Asn Met Glu Ile Ile Gln
                 20                  25                  30

Gly Ile Val Glu Ala Ala Lys Glu Glu Gln Ala Pro Leu Ile Leu Gln
             35                  40                  45

Val Ser Ala Gly Ala Arg Lys Tyr Ala Lys His Val Tyr Leu Val Lys
 50                  55                  60

Leu Val Glu Ala Ala Leu Glu Asp Ser Gly Asp Leu Pro Ile Ala Leu
 65                  70                  75                  80

His Leu Asp His Gly Glu Asp Phe Glu Ile Cys Lys Ala Cys Ile Asp
                 85                  90                  95

Gly Gly Phe Thr Ser Val Met Ile Asp Gly Ser Arg Leu Pro Phe Glu
                100                 105                 110

Glu Asn Ile Ala Leu Thr Lys Lys Val Val Glu Tyr Ala His Glu Arg
            115                 120                 125

Gly Val Val Glu Ala Glu Leu Gly Lys Leu Ala Gly Ile Glu Asp
        130                 135                 140

Asn Val Lys Val Ala Glu His Glu Ala Ala Phe Thr Asp Pro Asp Gln
145                 150                 155                 160
```

```
Ala Ala Glu Phe Val Glu Arg Thr Gly Val Asp Ser Leu Ala Val Ala
                165                 170                 175

Ile Gly Thr Ser His Gly Ala Tyr Lys Phe Lys Gly Glu Pro Arg Leu
            180                 185                 190

Asp Phe Glu Arg Leu Gln Arg Ile Val Glu Lys Leu Pro Lys Gly Phe
        195                 200                 205

Pro Ile Val Leu His Gly Ala Ser Ser Val Leu Pro Glu Phe Val Glu
    210                 215                 220

Met Cys Asn Lys Tyr Gly Gly Asn Ile Pro Gly Ala Lys Gly Val Pro
225                 230                 235                 240

Glu Asp Met Leu Arg Lys Ala Ala Glu Leu Gly Val Arg Lys Ile Asn
                245                 250                 255

Ile Asp Thr Asp Leu Arg Leu Ala Met Thr Ala Ala Ile Arg Lys His
            260                 265                 270

Leu Ala Glu His Pro Asp His Phe Asp Pro Arg Gln Tyr Leu Lys Asp
        275                 280                 285

Gly Arg Glu Ala Ile Lys Glu Met Val Lys His Lys Leu Arg Asn Val
    290                 295                 300

Leu Gly Cys Ser Gly Lys Ala Pro Glu Ile Leu Glu Glu Ile Lys Lys
305                 310                 315                 320

Asn Arg Gly

<210> SEQ ID NO 4
<211> LENGTH: 361
<212> TYPE: PRT
<213> ORGANISM: Kluyveromyces lactis NRRL Y-1140

<400> SEQUENCE: 4

Met Pro Ala Gln Asp Val Leu Thr Arg Lys Thr Gly Val Ile Val Gly
1               5                   10                  15

Asp Asp Val Lys Ala Leu Phe Asp Tyr Ala Lys Glu His Lys Phe Ala
                20                  25                  30

Ile Pro Ala Ile Asn Val Thr Ser Ser Thr Val Ala Ala Leu
            35                  40                  45

Glu Ala Ala Arg Asp Asn Lys Ser Pro Ile Ile Leu Gln Thr Ser Asn
    50                  55                  60

Gly Gly Ala Ala Tyr Phe Ala Gly Lys Gly Val Ser Asn Glu Gly Gln
65                  70                  75                  80

Asn Ala Ser Ile Arg Gly Ser Ile Ala Ala His Tyr Ile Arg Ser
                85                  90                  95

Ile Ala Pro Ala Tyr Gly Ile Pro Val Val Leu His Thr Asp His Cys
            100                 105                 110

Ala Lys Lys Leu Leu Pro Trp Phe Asp Gly Met Leu Lys Ala Asp Glu
        115                 120                 125

Glu Tyr Phe Ala Lys His Gly Glu Pro Leu Phe Ser Ser His Met Leu
    130                 135                 140

Asp Leu Ser Glu Glu Thr Asp Glu Glu Asn Ile Gly Leu Cys Val Lys
145                 150                 155                 160

Tyr Phe Thr Arg Met Ala Lys Ile His Gln Trp Leu Glu Met Glu Ile
                165                 170                 175

Gly Ile Thr Gly Gly Glu Glu Asp Gly Val Asn Asn Glu Gly Thr Ser
            180                 185                 190

Asn Asp Lys Leu Tyr Thr Thr Pro Glu Thr Val Phe Ser Val His Glu
        195                 200                 205
```

-continued

Ala Leu Ser Lys Ile Ser Pro Asn Phe Ser Ile Ala Ser Ala Phe Gly
    210                 215                 220

Asn Val His Gly Val Tyr Lys Ile Ala Ala Leu Lys Pro Glu Leu
225                 230                 235                 240

Leu Gly Thr Phe Gln Asp Tyr Ala Ala Lys Gln Leu Asn Lys Lys Ala
                245                 250                 255

Glu Asp Lys Pro Leu Tyr Leu Val Phe His Gly Gly Ser Gly Ser Ser
            260                 265                 270

Thr Lys Asp Phe His Thr Ala Ile Asp Phe Gly Val Lys Val Asn
275                 280                 285

Leu Asp Thr Asp Cys Gln Phe Ala Tyr Leu Ser Gly Ile Arg Asp Tyr
290                 295                 300

Val Leu Asn Lys Lys Asp Tyr Leu Met Thr Pro Val Gly Asn Pro Thr
305                 310                 315                 320

Gly Glu Asp Ser Pro Asn Lys Lys Tyr Tyr Asp Pro Arg Val Trp Val
                325                 330                 335

Arg Glu Gly Glu Lys Thr Met Ser Lys Arg Ile Thr Gln Ala Leu Glu
            340                 345                 350

Ile Phe Arg Thr Lys Gly Ala Leu Glu
            355                 360

<210> SEQ ID NO 5
<211> LENGTH: 485
<212> TYPE: PRT
<213> ORGANISM: Saccharomyces cerevisiae (strain ATCC 204508 / S288c)

<400> SEQUENCE: 5

Met Val His Leu Gly Pro Lys Lys Pro Gln Ala Arg Lys Gly Ser Met
1               5                   10                  15

Ala Asp Val Pro Lys Glu Leu Met Asp Glu Ile His Gln Leu Glu Asp
            20                  25                  30

Met Phe Thr Val Asp Ser Glu Thr Leu Arg Lys Val Val Lys His Phe
        35                  40                  45

Ile Asp Glu Leu Asn Lys Gly Leu Thr Lys Lys Gly Gly Asn Ile Pro
    50                  55                  60

Met Ile Pro Gly Trp Val Met Glu Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Ser Gly Asn His Thr Phe Asp Thr Thr Gln Ser Lys Tyr
            100                 105                 110

Lys Leu Pro His Asp Met Arg Thr Thr Lys His Gln Glu Glu Leu Trp
        115                 120                 125

Ser Phe Ile Ala Asp Ser Leu Lys Asp Phe Met Val Glu Gln Glu Leu
    130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190

Gln Asn Glu Ile Ser Lys Arg Glu Leu Pro Ile Glu Ile Val Ala Leu
        195                 200                 205

Ile Asn Asp Thr Val Gly Thr Leu Ile Ala Ser Tyr Tyr Thr Asp Pro
    210                 215                 220

```
Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
                245                 250                 255

Asp Ile Pro Ser Asn Ser Pro Met Ala Ile Asn Cys Glu Tyr Gly Ser
            260                 265                 270

Phe Asp Asn Glu His Leu Val Leu Pro Arg Thr Lys Tyr Asp Val Ala
            275                 280                 285

Val Asp Glu Gln Ser Pro Arg Pro Gly Gln Gln Ala Phe Glu Lys Met
        290                 295                 300

Thr Ser Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

Lys Gln Pro Tyr Ile Met Asp Thr Ser Tyr Pro Ala Arg Ile Glu Asp
            340                 345                 350

Asp Pro Phe Glu Asn Leu Glu Asp Thr Asp Ile Phe Gln Lys Asp
            355                 360                 365

Phe Gly Val Lys Thr Thr Leu Pro Glu Arg Lys Leu Ile Arg Arg Leu
370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Lys Tyr Pro Gly Phe Lys Glu Ala Ala Ala
            420                 425                 430

Lys Gly Leu Arg Asp Ile Tyr Gly Trp Thr Gly Asp Ala Ser Lys Asp
            435                 440                 445

Pro Ile Thr Ile Val Pro Ala Glu Asp Gly Ser Gly Ala Gly Ala Ala
        450                 455                 460

Val Ile Ala Ala Leu Ser Glu Lys Arg Ile Ala Glu Gly Lys Ser Leu
465                 470                 475                 480

Gly Ile Ile Gly Ala
                485

<210> SEQ ID NO 6
<211> LENGTH: 486
<212> TYPE: PRT
<213> ORGANISM: Saccharomyces cerevisiae (strain ATCC 204508 / S288c)

<400> SEQUENCE: 6

Met Val His Leu Gly Pro Lys Lys Pro Gln Ala Arg Lys Gly Ser Met
1               5                   10                  15

Ala Asp Val Pro Lys Glu Leu Met Gln Gln Ile Glu Asn Phe Glu Lys
                20                  25                  30

Ile Phe Thr Val Pro Thr Glu Thr Leu Gln Ala Val Thr Lys His Phe
            35                  40                  45

Ile Ser Glu Leu Glu Lys Gly Leu Ser Lys Lys Gly Asn Ile Pro
        50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
                85                  90                  95

Val Lys Leu Gly Gly Asp Arg Thr Phe Asp Thr Thr Gln Ser Lys Tyr
```

-continued

```
            100                 105                 110
Arg Leu Pro Asp Ala Met Arg Thr Thr Gln Asn Pro Asp Glu Leu Trp
            115                 120                 125
Glu Phe Ile Ala Asp Ser Leu Lys Ala Phe Ile Asp Glu Gln Phe Pro
            130                 135                 140
Gln Gly Ile Ser Glu Pro Ile Pro Leu Gly Phe Thr Phe Ser Phe Pro
145                 150                 155                 160
Ala Ser Gln Asn Lys Ile Asn Glu Gly Ile Leu Gln Arg Trp Thr Lys
                165                 170                 175
Gly Phe Asp Ile Pro Asn Ile Glu Asn His Asp Val Val Pro Met Leu
            180                 185                 190
Gln Lys Gln Ile Thr Lys Arg Asn Ile Pro Ile Glu Val Val Ala Leu
            195                 200                 205
Ile Asn Asp Thr Thr Gly Thr Leu Val Ala Ser Tyr Tyr Thr Asp Pro
210                 215                 220
Glu Thr Lys Met Gly Val Ile Phe Gly Thr Gly Val Asn Gly Ala Tyr
225                 230                 235                 240
Tyr Asp Val Cys Ser Asp Ile Glu Lys Leu Gln Gly Lys Leu Ser Asp
                245                 250                 255
Asp Ile Pro Pro Ser Ala Pro Met Ala Ile Asn Cys Glu Tyr Gly Ser
            260                 265                 270
Phe Asp Asn Glu His Val Val Leu Pro Arg Thr Lys Tyr Asp Ile Thr
            275                 280                 285
Ile Asp Glu Glu Ser Pro Arg Pro Gly Gln Gln Thr Phe Glu Lys Met
            290                 295                 300
Ser Ser Gly Tyr Tyr Leu Gly Glu Ile Leu Arg Leu Ala Leu Met Asp
305                 310                 315                 320
Met Tyr Lys Gln Gly Phe Ile Phe Lys Asn Gln Asp Leu Ser Lys Phe
                325                 330                 335
Asp Lys Pro Phe Val Met Asp Thr Ser Tyr Pro Ala Arg Ile Glu Glu
            340                 345                 350
Asp Pro Phe Glu Asn Leu Glu Asp Thr Asp Asp Leu Phe Gln Asn Glu
            355                 360                 365
Phe Gly Ile Asn Thr Thr Val Gln Glu Arg Lys Leu Ile Arg Arg Leu
            370                 375                 380
Ser Glu Leu Ile Gly Ala Arg Ala Ala Arg Leu Ser Val Cys Gly Ile
385                 390                 395                 400
Ala Ala Ile Cys Gln Lys Arg Gly Tyr Lys Thr Gly His Ile Ala Ala
                405                 410                 415
Asp Gly Ser Val Tyr Asn Arg Tyr Pro Gly Phe Lys Glu Lys Ala Ala
            420                 425                 430
Asn Ala Leu Lys Asp Ile Tyr Gly Trp Thr Gln Thr Ser Leu Asp Asp
            435                 440                 445
Tyr Pro Ile Lys Ile Val Pro Ala Glu Asp Gly Ser Gly Ala Gly Ala
            450                 455                 460
Ala Val Ile Ala Ala Leu Ala Gln Lys Arg Ile Ala Glu Gly Lys Ser
465                 470                 475                 480
Val Gly Ile Ile Gly Ala
                485
```

<210> SEQ ID NO 7
<211> LENGTH: 33
<212> TYPE: DNA
<213> ORGANISM: Artificial Sequence

```
<220> FEATURE:
<223> OTHER INFORMATION: Primer

<400> SEQUENCE: 7
ggttatcgtt cagttcgcca acggtggtgc ttc                              33

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
gaagcaccac cgttggcgaa ctgaacgata acc                              33

<210> SEQ ID NO 9
<211> LENGTH: 33
<212> TYPE: DNA
<213> ORGANISM: Artificial Sequence
<220> FEATURE:
<223> OTHER INFORMATION: Primer

<400> SEQUENCE: 9
gcgtccttcg gtaacgtagc cggtgtttac aag                              33

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
cttgtaaaca ccggctacgt taccgaagga cgc                              33

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
cttatctgca gggtgcgctg ggtaacc                                     27

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
ggttacccag cgcaccctgc agataag                                     27

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13
tacgatccgc aggtatggct gcgtgccg                                    28
```

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
cggcacgcag ccatacctgc ggatcgta                                28

<210> SEQ ID NO 15
<211> LENGTH: 32
<212> TYPE: DNA
<213> ORGANISM: Artificial Sequence
<220> FEATURE:
<223> OTHER INFORMATION: Primer

<400> SEQUENCE: 15
gtcgactcta agattttga tttcgtaaaa cc                            32

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
gcggccgctt acagaacgtc gatcgcgtt                               29

<210> SEQ ID NO 17
<211> LENGTH: 31
<212> TYPE: DNA
<213> ORGANISM: Artificial Sequence
<220> FEATURE:
<223> OTHER INFORMATION: Primer

<400> SEQUENCE: 17
gtcgacgcaa tcgtttcagc agaaaaattt g                            31

<210> SEQ ID NO 18
<211> LENGTH: 29
<212> TYPE: DNA
<213> ORGANISM: Artificial Sequence
<220> FEATURE:
<223> OTHER INFORMATION: Primer

<400> SEQUENCE: 18
gcggccgctt aagctttgtt tgctgaacc                               29

<210> SEQ ID NO 19
<211> LENGTH: 27
<212> TYPE: DNA
<213> ORGANISM: Artificial Sequence
<220> FEATURE:
<223> OTHER INFORMATION: Primer

<400> SEQUENCE: 19
gtcgacccac ttgtaacaac caaagag                                 27

<210> SEQ ID NO 20
<211> LENGTH: 32
<212> TYPE: DNA
<213> ORGANISM: Artificial Sequence
<220> FEATURE:
<223> OTHER INFORMATION: Primer

```
<400> SEQUENCE: 20
gcggccgctt agcctctgtt cttcttaatc tc                                32

<210> SEQ ID NO 21
<211> LENGTH: 29
<212> TYPE: DNA
<213> ORGANISM: Artificial Sequence
<220> FEATURE:
<223> OTHER INFORMATION: Primer

<400> SEQUENCE: 21
gtcgacccag ctcaagacgt attgaccag                                    29

<210> SEQ ID NO 22
<211> LENGTH: 31
<212> TYPE: DNA
<213> ORGANISM: Artificial Sequence
<220> FEATURE:
<223> OTHER INFORMATION: Primer

<400> SEQUENCE: 22
gcggccgctt attccaaagc acccttagta c                                 31
```

ALDOLASE, ALDOLASE MUTANT, AND METHOD AND COMPOSITION FOR PRODUCING TAGATOSE BY USING SAME

CROSS-REFERENCE TO RELATED APPLICATIONS

This application is a national phase entry under 35 U.S.C. § 371 of International Patent Application PCT/KR2014/006850, filed Jul. 25, 2014, designating the United States of America and published as International Patent Publication WO 2015/016544 A1 on Feb. 5, 2015, which claims the benefit under Article 8 of the Patent Cooperation Treaty to Korean Patent Application Serial Nos. 10-2014-0093443 filed Jul. 23, 2014, 10-2014-0001709 filed Jan. 7, 2014, and 10-2013-0089588 filed Jul. 29, 2013.

TECHNICAL FIELD

This disclosure relates to aldolase, an aldolase mutant, and a method for producing tagatose and a composition for producing tagatose using the same.

BACKGROUND

Generally, tagatose (D-tagatose) is a $C_4$ epimer of fructose (D-fructose) and has a sugar content of 92% relative to sugar but it is a low-calorie sweetener having a caloric value of 1.5 kcal/g, which is about 30% of sugar. Additionally, tagatose is a non-caloric sweetener with little or no metabolism occurring during the in-vivo absorption process. About 15% to 20% of the amount of tagatose ingested is absorbed into the body, but this absorption is due to the decomposition by the microorganisms in the large intestine, not by self-digestion capabilities in humans, and, thus, does not affect the blood glucose levels. Accordingly, it is expected to provide a blood glucose level-controlling effect to diabetic patients, and is known to provide foods for enteric microorganisms, thereby helping with excretion activity by microorganisms. Tagatose has the functional characteristics of not causing tooth decay and, thus, is a healthy sweetener instead of sugar to be safely included in chocolate, gums, bread, candies, and the like, that are favored by children so that they can ingest without worries, having been highlighted as a material that can contribute to the prevention of diseases due to excess sugar intake. Additionally, tagatose has a boiling point of 134° C. and a pH of 2 to 7, and is, thus, highly stable against heat and pH. Therefore, tagatose is not readily destroyed, unlike most artificial sweeteners, but has physical and chemical properties most similar to that of sugar. When it is heated, the characteristic of browning reaction is ketose, which is similar to that of fructose, and thus has an important characteristic as a sugar substitute.

For these reasons, tagatose has been highlighted as a food supplement and a diet sweetener in the food industry, and there is a growing need for the development of a method for efficiently producing tagatose. This is because tagatose is a rare sugar included in dairy products or a few plants in a small amount and it cannot be synthesized by a chemical method. At present, tagatose is being produced by isomerization of galactose via a bioconversion method using L-arabinose isomerase. However, the supply of galactose is unstable and its cost varies greatly depending on the change in the market of dairy products, thus causing difficulty in securing a steady and large amount of product.

Accordingly, to solve these problems, studies have actively focused on developing a method of producing tagatose using an enzyme based on substrates such as glucose or fructose, which has a low cost and steady supply.

Until now, a single enzyme reaction that can produce tagatose from fructose by a single enzyme reaction was unknown. In the case of a single enzyme, little or no conversion occurred by the mechanisms of enzymes for epimerization known so far and the production yield obtained therefrom was significantly low, thus making it insufficient for industrialization.

See Korean Patent Application No. 10-2001-0080711.

BRIEF SUMMARY

Described is an enzyme useful in a method for preparing tagatose with high yield using fructose as a substrate.

Also provided is a method of preparing tagatose with high yield using fructose as a substrate.

Also provided is a composition for preparing tagatose with high yield using fructose as a substrate.

Also provided is a composition that can mediate epimerization at $C_4$ of a monosaccharide including fructose 1,6-diphosphate aldolase as an active ingredient.

In an exemplary embodiment of this disclosure, the fructose 1,6-diphosphate aldolase is preferably one of the enzymes represented by the amino acid sequences of SEQ ID NOS: 1 to 4, or a fructose 1,6-diphosphate aldolase having similar activity with one or more mutations in these amino acid sequences, such as by substitution, deletion, inversion, and/or translocation, or mediating the epimerization of the $C_4$ of a different monosaccharide.

Additionally, this disclosure provides a method of epimerizing the $C_4$ of a monosaccharide by treating with fructose 1,6-diphosphate aldolase.

Additionally, this disclosure provides a composition for producing tagatose including fructose 1,6-diphosphate aldolase as an active ingredient.

In an exemplary embodiment of this disclosure, the fructose 1,6-diphosphate aldolase is preferably one of the enzymes represented by the amino acid sequences of SEQ ID NOS: 1 to 4, or a fructose 1,6-diphosphate aldolase having a similar activity with one or more mutations in these amino acid sequences, such as substitution, deletion, inversion, and/or translocation, or other fructose 1,6-diphosphate aldolase capable of producing tagatose.

Additionally, the disclosure provides a method of producing tagatose from fructose including reacting fructose 6-phosphate by adding aldolase thereto.

Additionally, this disclosure provides a composition including tagatose produced by the production method of this disclosure as an active ingredient.

Additionally, the disclosure provides a food composition including tagatose, which can be produced using tagatose 6-phosphate produced by the method of the disclosure, as an active ingredient.

In an exemplary embodiment of this disclosure, the food is preferably beverages, chocolate, gums, bread, candies, dairy products, animal products, and the like, but is not limited thereto.

This disclosure provides proteins represented by amino acid sequences SEQ ID NOS: 1, 2, 3, and 4, which possess the activity of epimerization of fructose 6-phosphate.

Additionally, a gene encoding proteins is provided having the activity of epimerization of fructose 6-phosphate, represented by amino acid SEQ ID NOS: 1, 2, 3, and 4.

Additionally, a recombinant expression vector including the above gene is provided.

Furthermore, this disclosure provides a method for producing tagatose by providing a method for producing tagatose 6-phosphate, which is characterized by reacting a protein with fructose 6-phosphate.

Additionally, this disclosure provides a composition for producing tagatose including a mutant of fructose 1,6-bisphosphate aldolase as an active ingredient.

In an exemplary embodiment of this disclosure, the fructose 1,6-bisphosphate aldolase is preferably an enzyme selected from the enzymes consisting of the amino acids represented by SEQ ID NOS: 1 to 4, but is not limited thereto.

In another exemplary embodiment of this disclosure, the mutant is preferably a substitution of one or more residues at positions of 332, 314, 227, and 62 of fructose aldolased enzyme comprised of SEQ ID NO: 1, wherein the residue at position 332 is substituted from arginine to glutamine, the residue at position 314 is substituted from glutamine to alanine, the residue at position 227 is substituted from histidine to alanine, and the residue at position 62 is substituted from serine to alanine.

However, all mutants with an increased activity of the corresponding enzyme compared with that of the wild-type enzyme, by inducing a mutation in other wild-type enzymes of fructose 1,6-bisphosphate aldolase, can belong to the protective scope of this disclosure. For example, the mutant with an increased activity of the corresponding enzyme compared with that of the wild-type enzyme, by inducing a mutation in any one of the enzymes represented by SEQ ID NOS: 2 to 4, certainly belongs to the protective scope of the disclosure.

In still another exemplary embodiment of this disclosure, the above composition preferably further includes hexokinase and phytase, but is not limited thereto.

Additionally, the disclosure provides a method for producing tagatose including treating a mutant of the fructose 1,6-bisphosphate aldolase of this disclosure with fructose-6-phosphate.

In an exemplary embodiment of this disclosure, the fructose-6-phosphate is preferably obtained by treating fructose or a fructose-containing material with hexokinase but, when it is provided by other chemical syntheses, it will also belong to the scope of the disclosure.

In another exemplary embodiment of the disclosure, the method preferably further includes converting the tagatose 6-phosphate into tagatose by acting phytase thereon, but the tagatose 6-phosphate may have its phosphate group removed by a different enzyme or chemical method.

Additionally, this disclosure provides an enzyme for a mutant enzyme of fructose 1,6-bisphosphate aldolase, one of the enzymes selected from the enzymes consisting of the amino acids represented by SEQ ID NOS: 1 to 4.

Additionally, the disclosure provides a gene encoding a mutant of this disclosure.

In an exemplary embodiment of the disclosure, hexokinase may be represented by the amino acid sequence of SEQ ID NO: 5 or 6, but all corresponding enzymes having the effect to be achieved in this disclosure belong to the protective scope of the disclosure.

According to this disclosure, the productivity of tagatose was increased using the enzyme for epimerizing the $C_4$ of phosphate sugar and the resolution of the problems that occur when fermentation was performed using the producing method through the enzyme reaction of the cell itself. In particular, there has been no precedent example of producing tagatose from fructose, and the first such production was attempted in the embodiments of this disclosure. Additionally, a yield close to 80% of tagatose can be obtained from fructose by a cocktail reaction.

This disclosure will be described in more detail hereinbelow.

In particular, unless defined otherwise, the technical and scientific terms as used herein will refer to those that are commonly understood by a skilled person in the art.

Additionally, repeated explanations on the technical constitutions and actions equivalent to those of the conventional ones will be omitted hereinbelow.

The characteristics of fructose 1,6-bisphosphate aldolase were confirmed by cloning a gene corresponding to the fructose 1,6-bisphosphate aldolased enzyme or protein derived from *E. coli* K-12, whose characteristics have not yet been confirmed in substrates other than the natural substrate, i.e., fructose 1,6-bisphosphate, and culturing a microorganism transformed with an expression vector including the gene, followed by overexpression of the fructose 1,6-bisphosphate aldolase.

As a result, this disclosure confirmed that the enzyme has the substrate specificity of epimerizing the $C_4$ of the fructose 6-phosphate and, thus, relates to producing tagatose 6-phosphate using the above enzyme and then treating with a commercial phytase, thereby producing tagatose.

More specifically, the gene for the known enzyme, fructose 1,6-bisphosphate aldolase, is already known, but those bacteria, such as *Escherichia coli* K-12, *Bacillus subtilis*, *Caldicellulosiruptor saccharolyticus*, and *Kluyveromyces lactis*, that have not been confirmed of their characteristics of epimerizing $C_4$ using fructose 6-phosphate, were used. The embodiments of this disclosure confirm that all of these enzymes have the activity of converting fructose 6-phosphate into tagatose 6-phosphate.

In particular, for the confirmation of the characteristics of the enzyme, the disclosure preferably uses an enzyme obtained by: acquiring the gene for fructose 1,6-bisphosphate aldolase in a large amount by polymerase chain reaction (PCR) from a bacterial strain including the gene for the known fructose 1,6-bisphosphate aldolase, which has been evaluated based on its nucleotide sequence by the previous experiment and named accordingly without at all confirming the functional characteristics; inserting the gene into an appropriate expression vector to construct a recombinant vector including the fructose 1,6-bisphosphate aldolase gene; culturing a transformed bacteria, which was prepared by transforming the recombinant vector into an appropriate microorganism, in a fermentation medium and overexpressing the enzyme; and purifying.

Additionally, the method of this disclosure for producing tagatose consists of three steps of obtaining fructose 6-phosphate by treating fructose 1,6-bisphosphate aldolase, which was commonly called fructose 1,6-bisphosphate aldolased enzyme, with hexokinase; obtaining tagatose 6-phosphate by reacting the fructose 6-phosphate with a substrate; and obtaining tagatose by treating the tagatose 6-phosphate with phytase.

Additionally, the fructose 1,6-bisphosphate aldolase enzyme used in producing tagatose of the disclosure is not limited to the amino acid sequences represented by SEQ ID NOS: 1 to 4. Any amino acid sequence may be used as long as it can convert fructose 6-phosphate into tagatose 6-phosphate, even when there is substitution, insertion, or deletion in a part of the amino acid sequences described in SEQ ID NOS: 1 to 4.

Additionally, in the method of this disclosure for producing tagatose, the expression vector to be used in cloning the gene for fructose 1,6-bisphosphate aldolase may be any vector including RSF Duet-1 that has been used in gene recombination. It is preferable to use E. coli BL21(DE3) as the bacterial strain to be transformed with the recombinant vector, but any bacterial strain that can produce an active protein via overexpression of a desired gene after being transformed with a gene recombinant vector may be used.

More specifically, regarding the cultivation of a microorganism in the disclosure, E. coli BL21(DE3) [Escherichia coli BL21(DE3)] was used as the recombinant bacterial strain to obtain fructose 1,6-bisphosphate aldolase. LB was used as a culture medium for producing the microorganism, and a medium including 10 g/L of glycerol, 1 g/L of peptone, 30 g/L of yeast extract, 0.14 g/L of potassium diphosphate, and 1 g/L of monosodium phosphate was used as the medium for producing the enzyme. For the large-scale production of fructose 1,6-bisphosphate aldolase, it is preferable to inoculate the frozen-stored strain BL21(DE3) into a 250-mL flask including 50 mL of an LB medium, culture the bacterial strain in a shaking water bath at 37° C. until the absorbance at 600 nm reaches 2.0, add the culture into a 7-L fermenter (Biotron, Korea) including 5 L of a fermentation medium and culture until the absorbance at 600 nm reaches 2.0, add with 1 mM IPTG to induce the production of the overexpressing enzyme, while maintaining the stirring speed at 500 rpm, aeration of 1.0 vvm, and the culture temperature at 37° C. during the process.

Additionally, for the purification of the fructose 1,6-bisphosphate aldolase produced by overexpression, the purified enzyme of this disclosure is preferably obtained by the following process: centrifuging the culture of the transformed bacterial strain at 6,000×g at 4° C. for 30 minutes; washing the resulting cells twice with 0.85% NaCl, adding the cells in a cell lysate buffer solution (50 mM $NaH_2PO_4$, 300 mM NaCl, pH 8.0) including 1 mg/mL of lysozyme, and placing in ice for 30 minutes; and crushing the cells in the solution by a French press at 15,000 $lb/in^2$ and removing the cell lysate by centrifugation at 13,000×g at 4° C. for 20 minutes, while purifying the supernatant by filtering through a 0.45-μm filter paper. In particular, the purification process is performed in a low-temperature room via fast protein liquid chromatography (FPLC), in which the filtrate is applied to a HISTRAP® HP column equilibrated with a 50-mM Tris-HCl buffer solution including 300 mM NaCl (pH 8.0) and 10 mM imidazole. Preferably, the enzyme attached to the column after washing the column with the same buffer solution is eluted by flowing a solution, which includes imidazole, at a concentration with a gradient from 10 mM to 200 mM, at a rate of 1 mL/minute. Preferably, a fraction of the thus-eluted enzyme with an activity is added into a HiPREP® 16/60 desalting resin column equilibrated with a 50-mM Tris-HCl buffer solution (pH 8.5). The added protein is washed at a rate of 6 mL/minute. The accumulated enzyme solution is added into a Sephacryl S-100 HR column equilibrated with 50 mM Tris-HCl buffer solution including 0.15 M sodium chloride (pH 8.5) to elute the accumulated enzyme at a rate of 6.6 mL/minute. The eluted solution is finally dialyzed in a 50-mM Tris-HCl buffer solution to be used.

Additionally, the thus-obtained fructose 1,6-bisphosphate aldolase according to this disclosure is a monomer having a molecular weight of 78 kDa, and is a metalloenzyme whose activation is controlled by metal ions.

In particular, it is preferable that the fructose 1,6-bisphosphate aldolase and fructose 6-phosphate are reacted at a ratio of 55% to 75% (w/w) at 50° C. (pH 8.5) considering the production yield of tagatose 6-phosphate. This is because the production yield of tagatose 6-phosphate was excellent when the concentration of the substrate for fructose was in the range of 55% to 75% (w/w), and the above pH and the temperature were the optimum conditions for the fructose 1,6-bisphosphate aldolased enzyme.

Meanwhile, the cocktail reaction of this disclosure is a method for producing tagatose in a large scale by reacting fructose within a cell using hexokinase, fructose 1,6-bisphosphate aldolased enzyme, and phytase. It is preferable to use kinase and fructose 1,6-bisphosphate aldolase expressed in a large amount by overexpressing them within a cell. This is because the intracellular environment enables maintaining the activity of an overexpressed enzyme for a long period of time and regenerating cofactors necessary for reactions. The E. coli that can be used in the disclosure may be any E. coli as long as it can overexpress enzymes.

Since the method of producing tagatose according to this disclosure uses enzymes obtained from microorganisms, it is environment-friendly, requires only a simple enzyme-fixing process, and can convert the production of tagatose from fructose in a method that has not been done previously, while greatly reducing production cost and maximizing the production effect.

Additionally, the tagatose produced in a large-scale method as described above may be effectively used by being added into functional foods and pharmaceutical drugs.

Hereinafter, this disclosure will be explained in more detail by the exemplary embodiments. However, it should be obvious to a skilled person in the art that the exemplary embodiments disclosed herein should not be construed as limiting the scope of the disclosure, but covering various alternatives and modifications as well as the exemplary embodiments within the ideas and scope of the disclosure. Accordingly, the appended claims should be appropriately interpreted to comply with the spirit and scope of this disclosure.

As described above, the characterization of novel enzymes according to the disclosure can provide an advantage in that the enzymes can be used after selection to be suitable for various production environments based on the similarities in characteristics between enzymes and the identity and conversion rate possessed by each enzyme.

Additionally, the disclosed method of producing tagatose is environment-friendly because only the enzymes obtained from microorganisms are used, requiring only a simple enzyme-fixing process. Compared with the conventional methods of tagatose production, the disclosed method uses only low-cost substrates while having a significantly higher yield, thus, markedly reducing production cost and maximizing production effect.

BRIEF DESCRIPTION OF THE DRAWINGS

FIGS. 2 to 4 illustrate the comparison results of phylogenetic trees and amino acid sequences with fructose 1,6-diphosphate aldolased enzyme derived from Escherichia coli K-12, regarding the selection of fructose 1,6-diphosphate aldolase of Streptococcus thermophilus, Caldicellulosiruptor saccharolyticus, and Kluyveromyces lactis introduced in the disclosure.

*cus*, and *Kluyveromyces lactis* after reacting with 5 mM fructose 6-phosphate at pH 8.5 at 50° C. for 1 hour.

Figure 1:
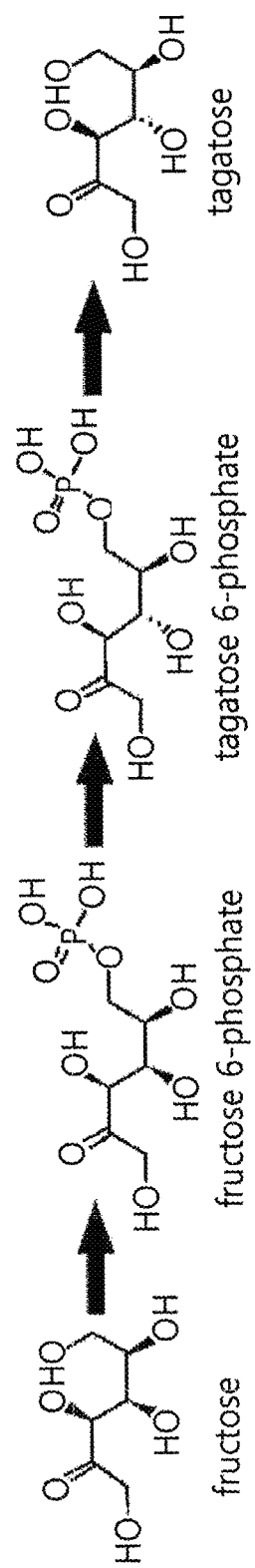
FIG. 1 is a schematic diagram illustrating the production of tagatose from fructose by a cocktail reaction introduced in this disclosure.
Figure 4:
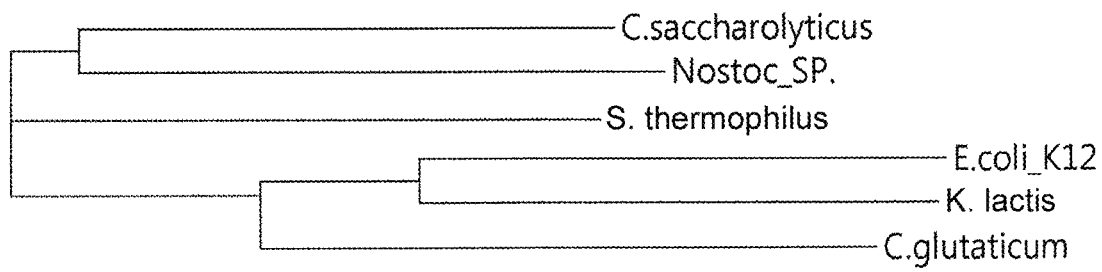
Figure 5:
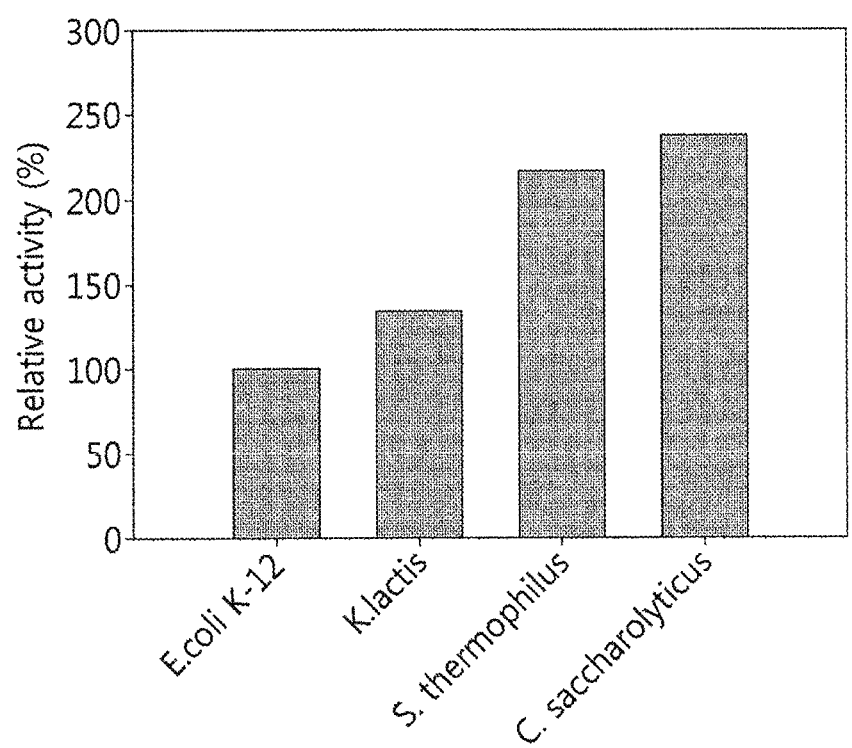
FIG. 5 is a graph illustrating the relative activities of fructose 1,6-diphosphate aldolased enzyme derived from Escherichia coli K-12 and fructose 1,6-diphosphate aldolased enzyme of fructose 1,6-diphosphate aldolase of Streptococcus thermophilus, Caldicellulosiruptor saccharolyti-
Figures 6, 7:
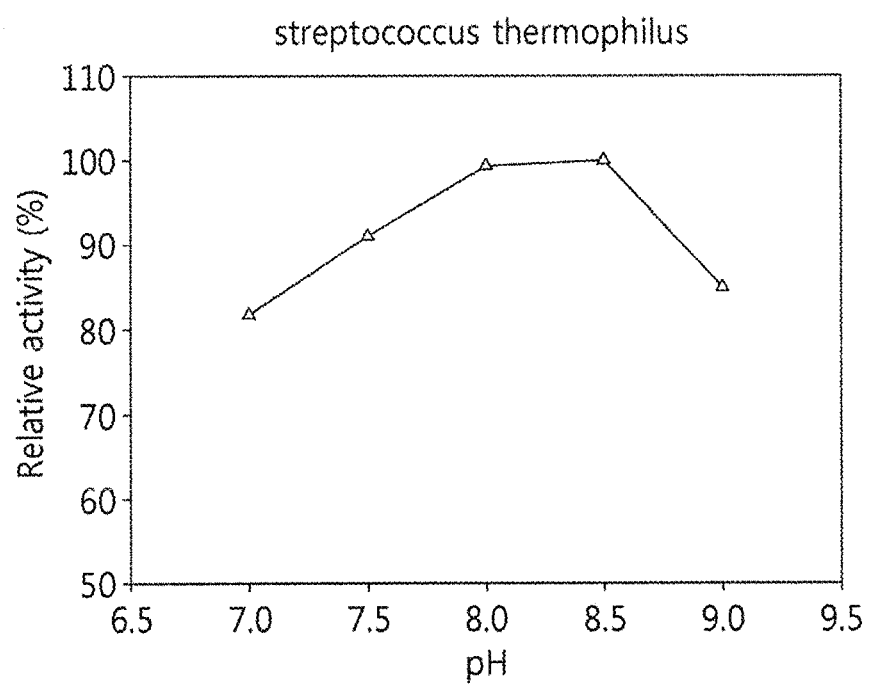

FIG. 6 is a graph illustrating comparison results of the metal specificity of fructose 1,6-diphosphate aldolases of this disclosure.

Figure 8:
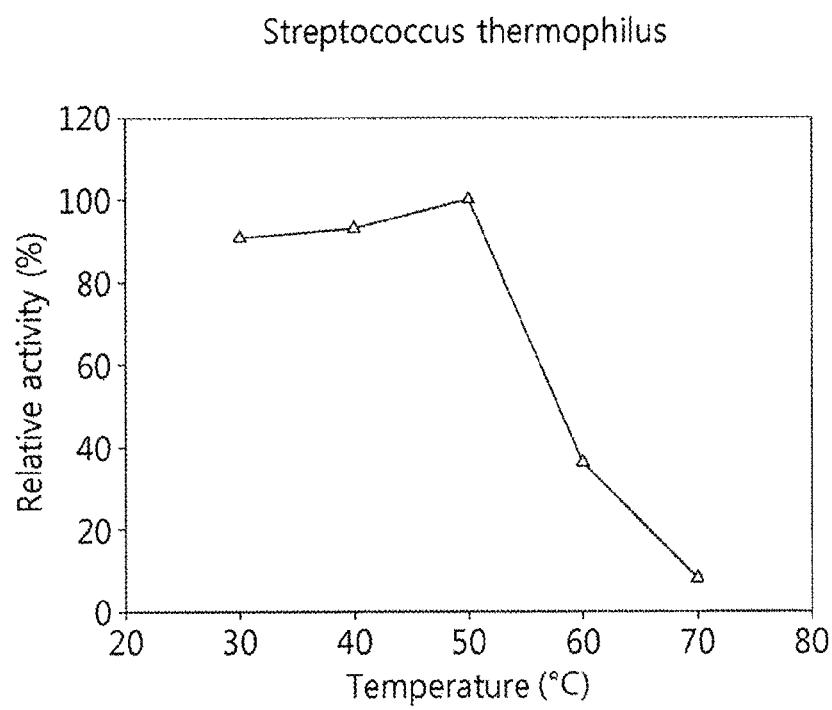
Figure 9:
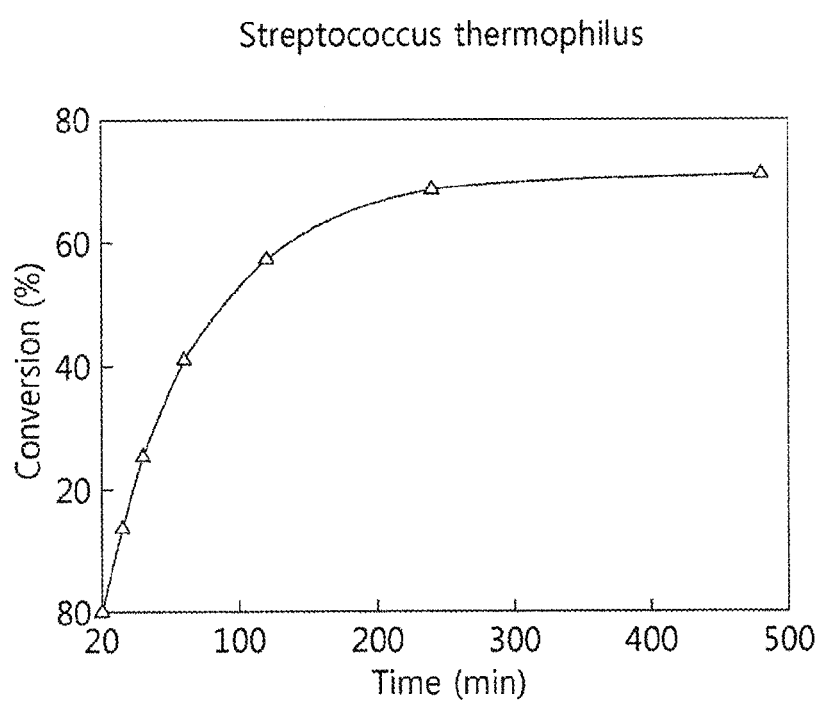

FIGS. 7 to 9 are graphs illustrating the relative activity and conversion (FIG. 9) of tagatose 6-phosphate in fructose 6-phosphate according to an enzyme optimum pH (FIG. 7) and optimum temperature (FIG. 8) for fructose 1,6-diphosphate aldolase of *Streptococcus thermophilus*, respectively.

Figure 10:
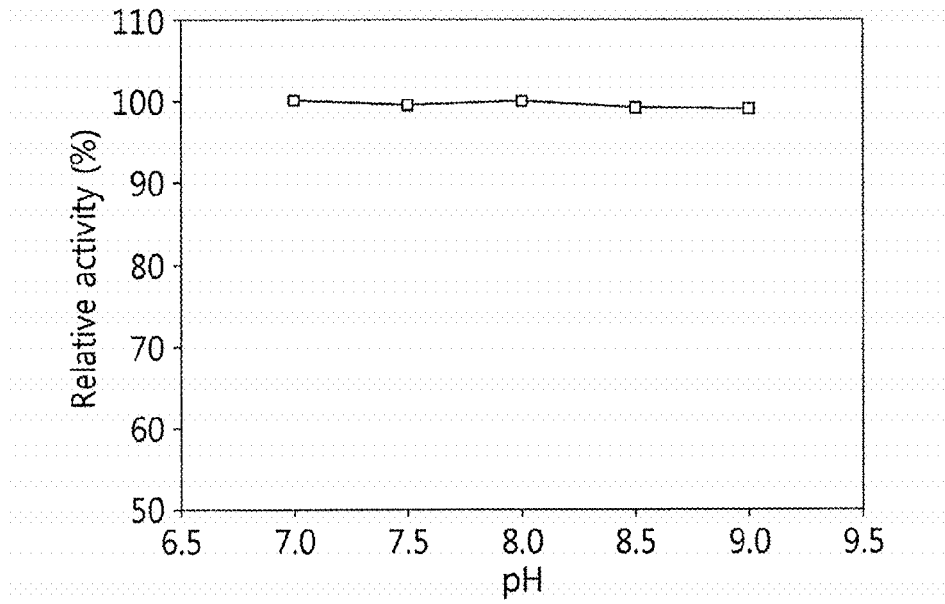
Figure 11:
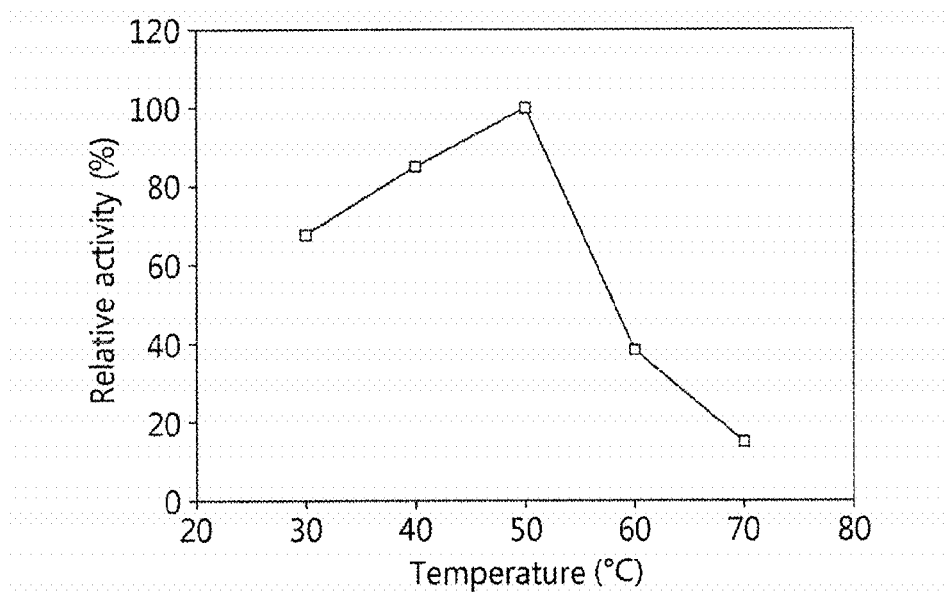
Figure 12:
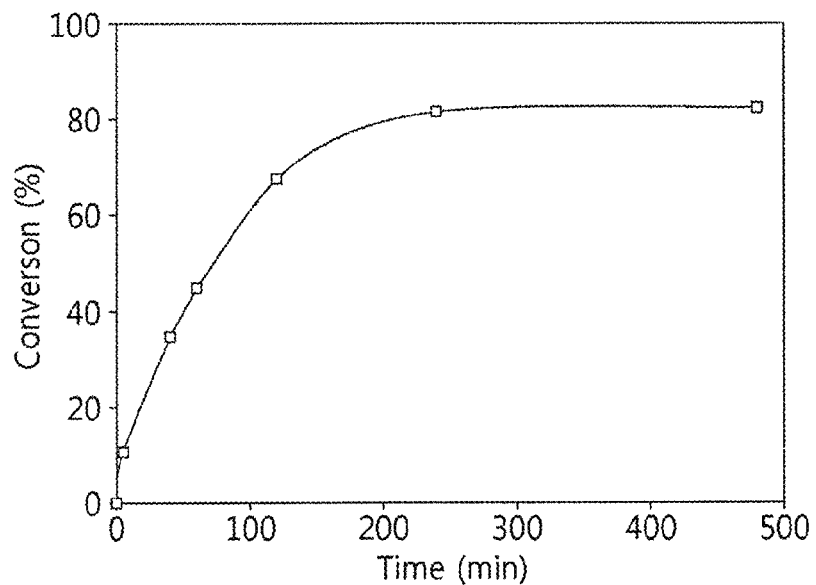

FIGS. 10 to 12 are graphs illustrating the relative activity and conversion (FIG. 12) of tagatose 6-phosphate in fructose 6-phosphate according to an enzyme optimum pH (FIG. 10) and optimum temperature (FIG. 11) for fructose 1,6-diphosphate aldolase of *Caldicellulosiruptor saccharolyticus*, respectively.

Figure 13:
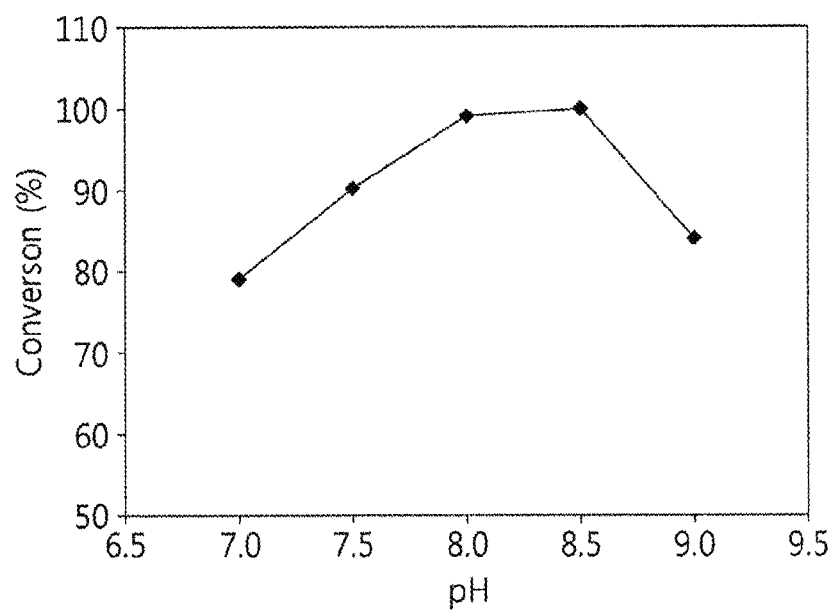
Figure 14:
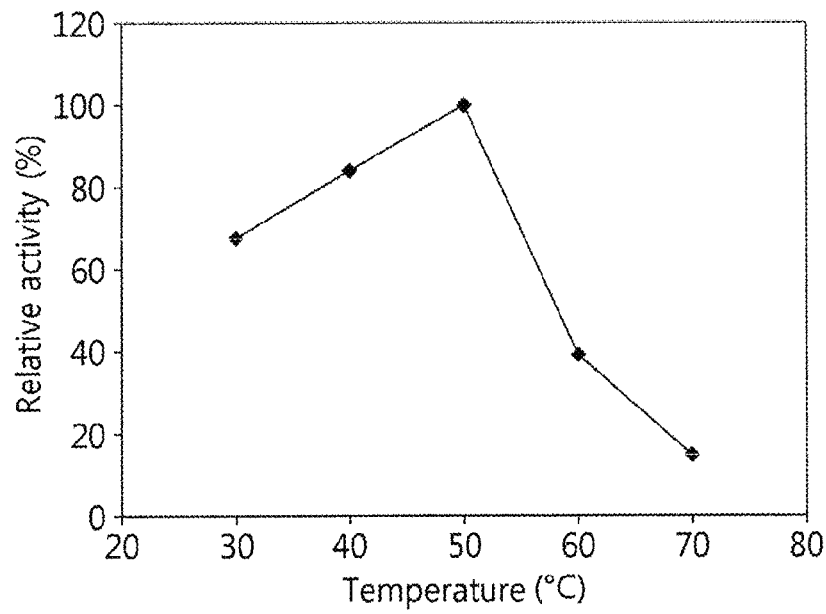
Figure 15:
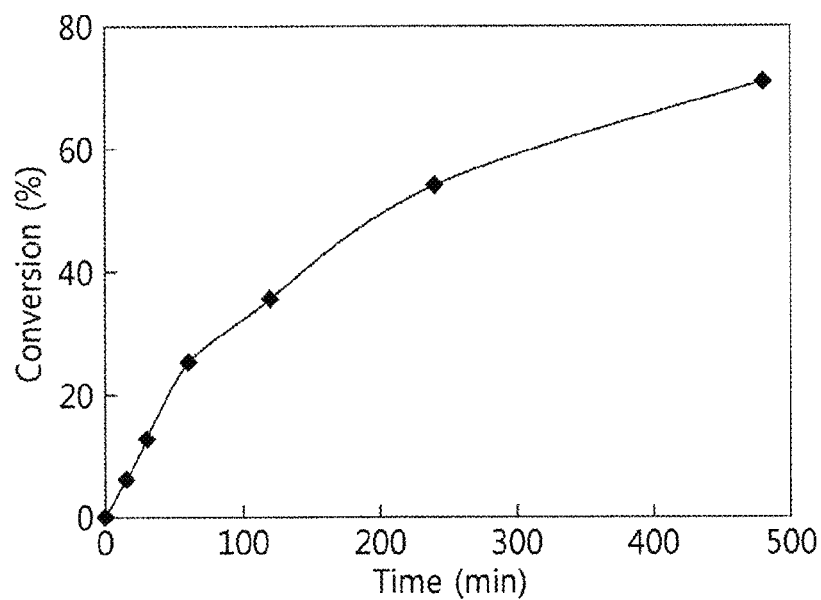

FIGS. 13 to 15 are graphs illustrating the relative activity and conversion (FIG. 15) of tagatose 6-phosphate in fructose 6-phosphate according to an enzyme optimum pH (FIG. 13) and optimum temperature (FIG. 14) for fructose 1,6-diphosphate aldolase of *Kluyveromyces lactis*, respectively.

Figure 16:
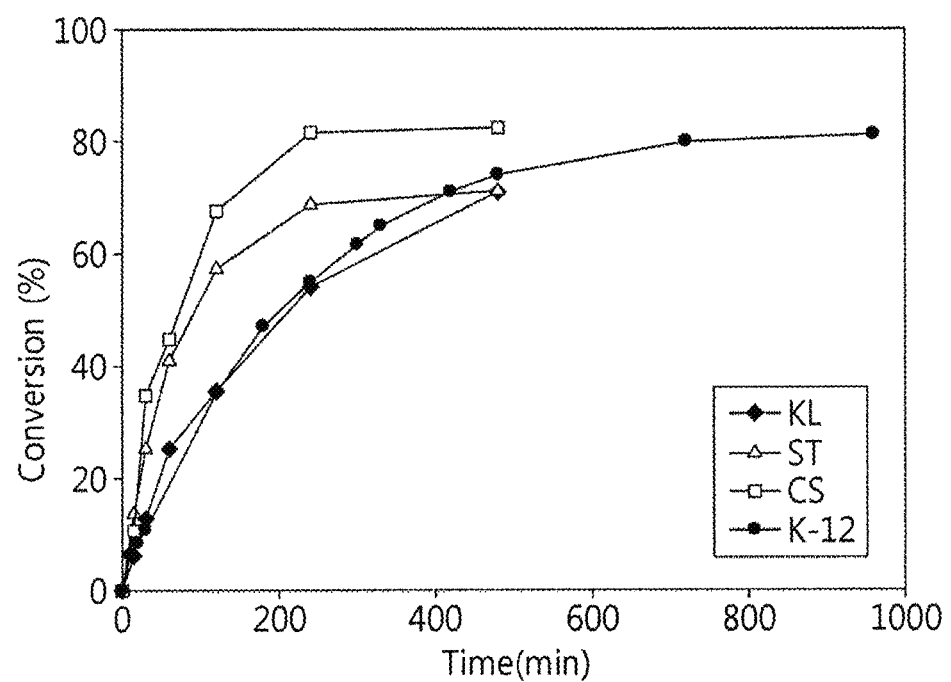

FIG. 16 is a graph illustrating the results of the conversion of fructose 6-phosphate into tagatose 6-phosphate using each of the fructose 1,6-diphosphate aldolases used in the disclosure. The fructose 1,6-diphosphate aldolase of *Kluyveromyces lactis* exhibited an activity similar to that of the enzyme derived from *Escherichia coli* K-12, and the enzyme derived from *Streptococcus thermophilus* exhibited a fast initial conversion but exhibited a slower conversion of 71%. The enzyme derived from *Caldicellulosiruptor saccharolyticus* exhibited a conversion of about 80%, similar to that of the enzyme derived from *Escherichia coli* K-12, and a fast initial conversion.

Figure 17:
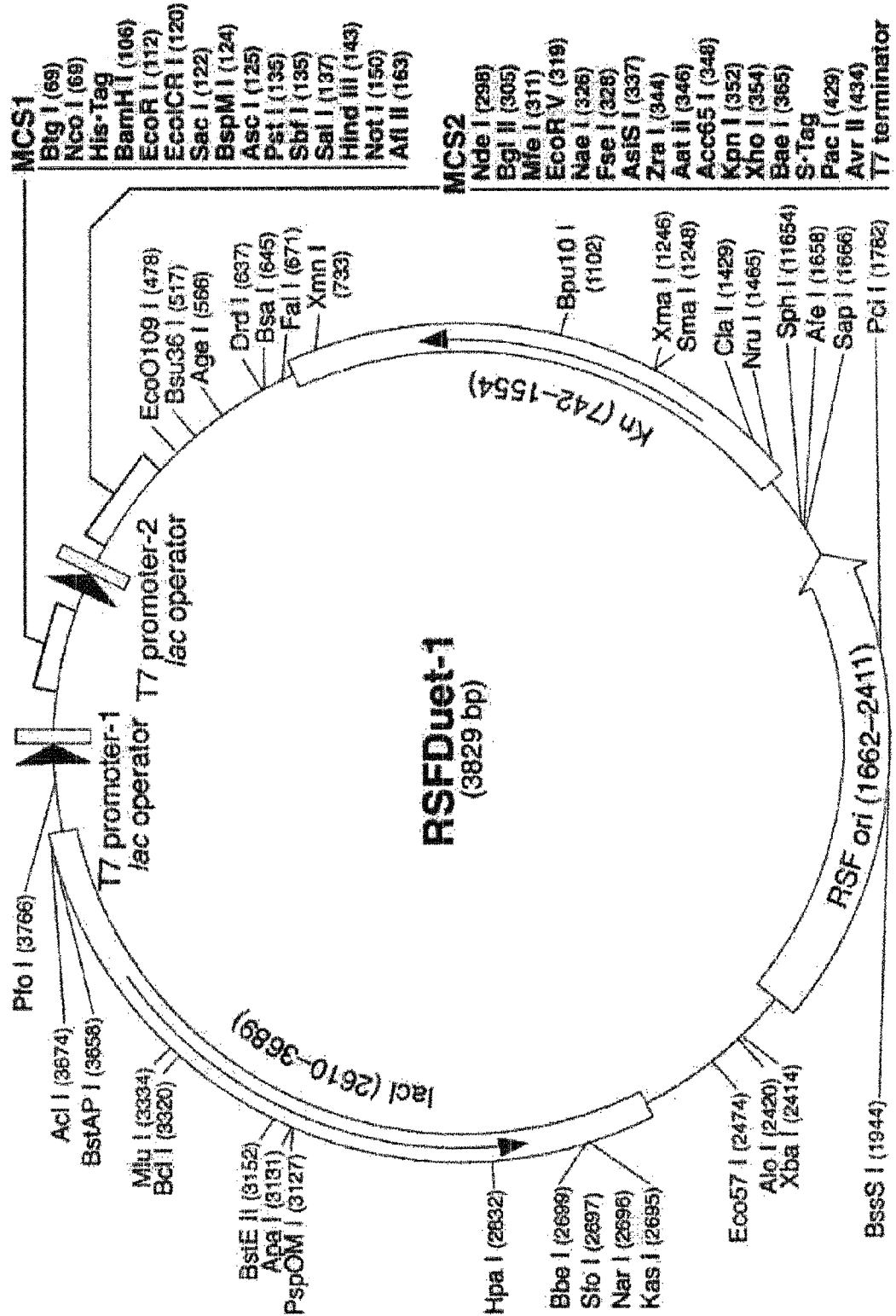

FIG. 17 is a schematic diagram of RSF Duet-1 vector system used in this disclosure and aims at cloning other enzymes along with fructose 1,6-diphosphate aldolase.

Figures 18, 19:
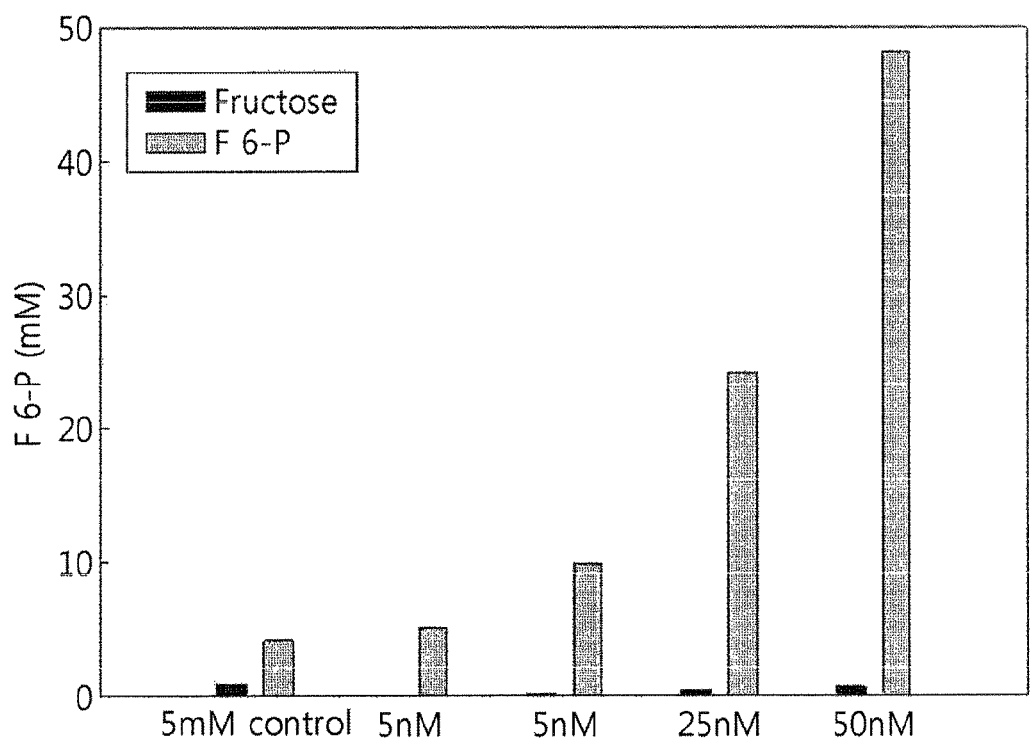

FIG. 18 is a graph illustrating the production activity obtained by reacting hexokinase derived from *Saccharomyces cerevisiae* with fructose in a concentration from 5 mM to 50 mM for 1 hour.

FIGS. 19 to 22 illustrate the metal specificity of fructose 1,6-diphosphate aldolase of *Escherichia coli* of the disclosure (FIG. 19), the conversion from fructose 6-phosphate into tagatose 6-phosphate according to an optimum pH for fructose 1,6-diphosphate aldolase of *Escherichia coli* (FIG. 20), and the conversion according to an optimum temperature (FIG. 21), respectively.

Figure 20:
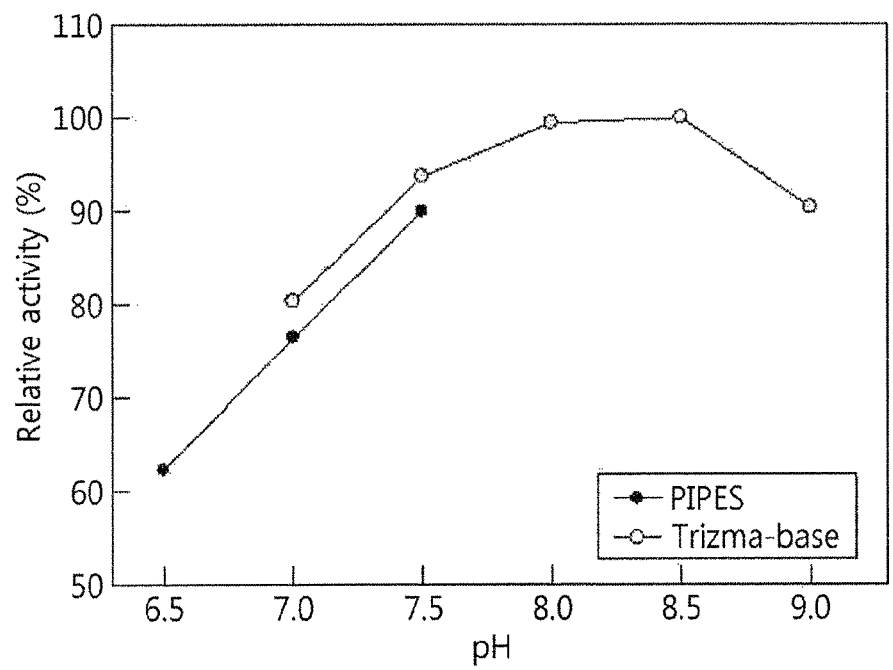
Figure 21:
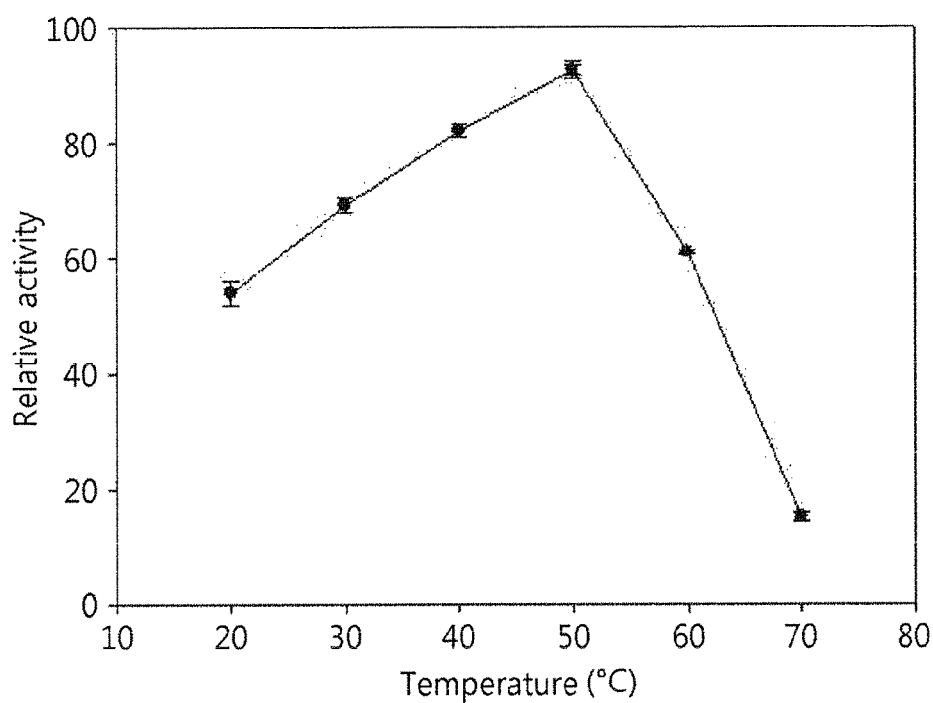
Figures 22, 23:
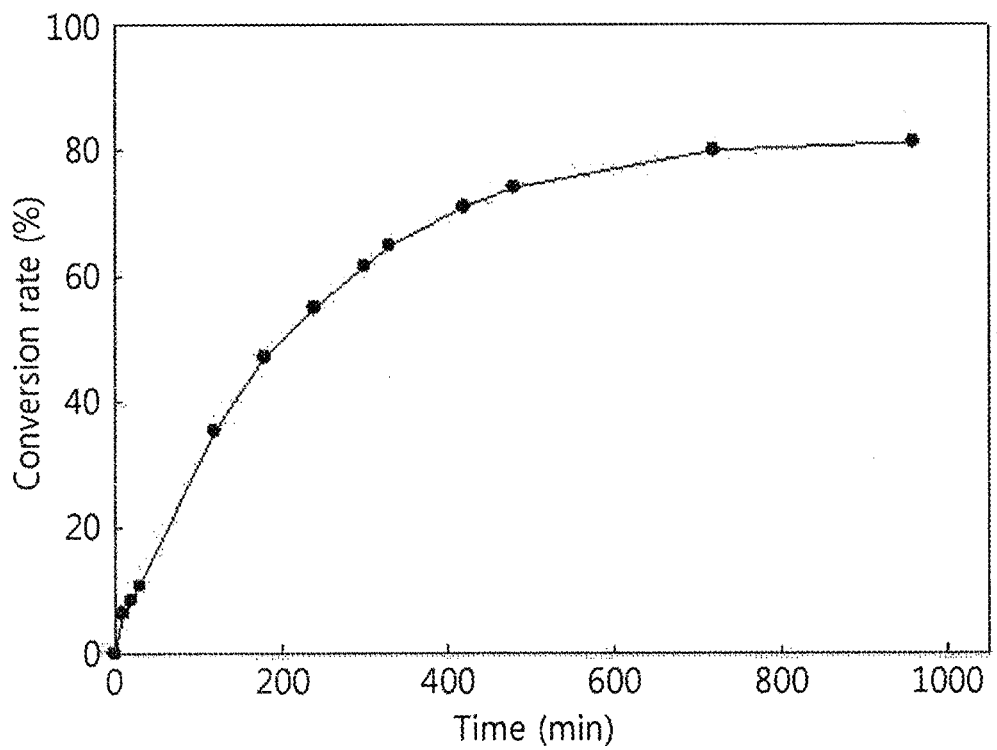

FIG. 22 is a graph illustrating the result of converting 10 mM fructose 6-phosphate into tagatose 6-phosphate under the optimum conditions confirmed in the results of FIGS. 19 to 21.

FIG. 23 lists the conversion into tagatose according to the concentration of phytase when reacting the tagatose 6-phosphate, which was converted in this disclosure, with phytase.

Figure 24:
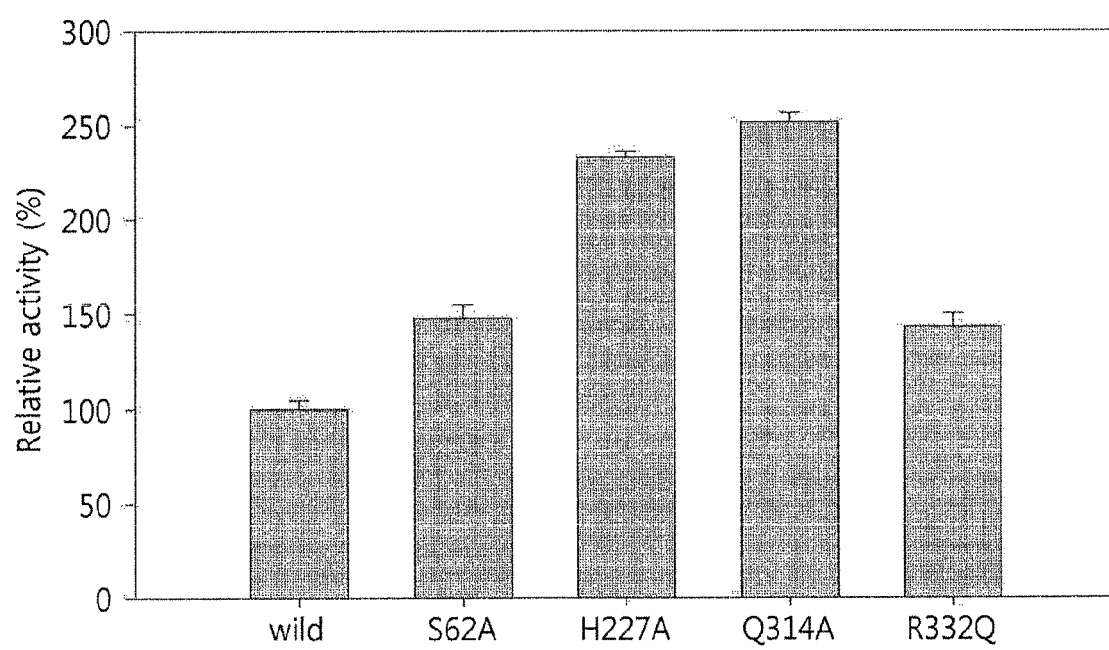

FIG. 24 is a graph illustrating the comparison result of enzyme activity between gene-mutating enzymes constructed in the disclosure and a wild-type enzyme, in which increased conversion rate and improved productivity are obtained by a faster conversion rate.

DETAILED DESCRIPTION

Hereinafter, the embodiments of this disclosure will be described in detail with reference to the Examples. However, the scope of the disclosure is not limited by these Examples.

Example 1. Large-Scale Production of Fructose 1,6-Diphosphate Aldolased Enzyme

Regarding fructose 1,6-diphosphate aldolase genes, DNA from *Escherichia coli* strain K-12, and each strain of *Streptococcus thermophilus, Caldicellulosiruptor saccharolyticus,* and *Kluyveromyces lactis* were suggested as genes for fructose 1,6-diphosphate aldolase, but they were obtained in a large scale by performing PCR amplification after designing primers (see Table 2) based on the nucleotide sequence of DNA of genes, which have never been identified, inserting the PCR product into an RSF Duet-1 vector [Novagen] using restriction enzymes Sal I and Not I to construct a recombinant vector, RSF Duet-1/fructose 1,6-diphosphate aldolase, followed by transforming the recombinant vector into *E. coli* BL21(DE3) by a conventional transformation method. Additionally, the *E. coli* BL21 strain was stored in liquid nitrogen prior to cultivation for a large-scale production.

Then, for a large-scale production of fructose 1,6-diphosphate aldolase, first, the frozen-stored BL21(DE3) strain was inoculated into a 250-mL flask including 50 mL of LB and seed cultured in a shaking water bath maintained at 37° C. until the absorbance at 600 nm reached 2.0, and the seed-cultured culture broth was subjected to a main cultivation by adding it into a 7-L fermentor (Biotron, Korea) including 5 L of a fermentation medium (10 g/L of glycerol, 1 g/L of peptone, 30 g/L of yeast extract, 0.14 g/L of potassium diphosphate, and 1 g/L of monosodium phosphate). In particular, the large-scale production of fructose 1,6-diphosphate aldolase was induced by adding 1 mM ITPG when the absorbance at 600 nm reached 2.0. Specifically, the stirring speed at 500 rpm, aeration of 1.0 vvm, and the culture temperature at 37° C. were maintained during the above process.

Example 2. Purification of Fructose 1,6-Diphosphate Aldolase

In order to accurately identify the characteristics of fructose 1,6-diphosphate aldolase, the enzyme was purified using affinity HisTrap® HP column, desalting HiPrep® 16/60, and gel filtration SEPHACRYL® S-100 HR column.

Example 3. Metal Specificity of Fructose 1,6-Diphosphate Aldolase

According to previous reports, fructose 1,6-diphosphate aldolase is involved in the conversion of 1,6-diphosphate substrate into dihydroxyacetone phosphate and glyceraldehyde 3-phosphate by metal zinc and improved titer. However, this disclosure confirmed that a metal salt effect does not result in increased titer when fructose 6-phosphate was applied as a substrate. In order to examine the metal salt effect, the enzyme activity was measured after treating with EDTA or adding 1 mM metal ions, as illustrated in figures below, and, in particular, the reaction was performed in a 50-mM PIPES buffer solution (pH 8.5) including 0.15% fructose and 0.05 U/mL of the enzyme at 50° C. for 30 minutes, and the enzyme activity was measured after stopping the reaction with 0.2 M HCl.

As a result, it was confirmed that the fructose 1,6-diphosphate aldolase of the disclosure exhibited no change in its activity by metal ions and, unlike that disclosed in previous reports, zinc ions were exhibited to be a metal enzyme that can significantly inhibit enzyme activity.

Example 4. Activity of Fructose 1,6-Diphosphate Aldolase According to Changes in pH and Temperature In the present Example, in order to examine the activity of fructose 1,6-diphosphate aldolase according to changes in pH and temperature, the enzyme and the substrate were reacted at various pH and temperatures to compare the enzyme activity. In particular, to examine the effect of pH, the reaction was performed in a 50-mM Trizma base buffer solution including 0.15% fructose 6-phosphate and 0.05 U/mL of the enzyme at a pH from 7.0 to 9.0. Specifically, the reaction was performed at 50° C. for 1 hour. Then, 0.2 M HCl was added to stop the reaction and the enzyme activity was measured. The results are illustrated in each figure.

Additionally, in order to examine the effect of temperature, the reaction was performed in a 50-mM Trizma base buffer solution (pH 8.5) including 0.15% fructose 6-phosphate and 0.05 U/mL of the enzyme at a temperature from 30° C. to 70° C. for 1 hour. Specifically, 0.2 M HCl was added to stop the reaction and the enzyme activity was measured. The results are illustrated in each figure. As a result, the optimum pH was exhibited to be 8.5, being similar in both *Streptococcus thermophilus* and *Kluyveromyces lactis*, and their activities were exhibited to be independent of pH. The optimum temperature for each of the enzymes was exhibited to be 50° C., and *Streptococcus thermophiles* also showed 91% of relative activity at 30° C.

Based on the above results, it was confirmed that the conversion of fructose 6-phosphate into tagatose 6-phosphate at optimum temperature and pH according to time zone could reach from 70% to 80%, and the results are illustrated in figures. However, regarding the above reaction, any reaction in any range according to the desired yield or reaction conditions may be applied without defining particular pH or temperature.

Example 5. Activity of Conversion from Fructose to Fructose 6-Phosphate by Hexokinase For the production of tagatose at high concentration, as the first step, fructose 6-phosphate was produced by reacting fructose at a concentration of from 5 mM to 50 mM with an equal amount of adenosine triphosphate (ATP) and hexokinase derived from *Saccharomyces cerevisiae*, and reacted with 250 U/mL of the enzyme included in a 50-mM Tris buffer solution (pH 7.5) at 30° C. for 60 minutes. Then, the enzyme activity was measured. The amount of fructose 6-phosphate production according to enzyme concentration is illustrated in FIG. 18. As a result, fructose 6-phosphate at a concentration of from 5 mM to 50 mM was produced, and this corresponds to 90% or higher of conversion.

The hexokinase used in this Example was lyophilized powder, H4502 Type F-300 purchased from Sigma Aldrich (130 U/mg protein (biuret), Sigma) and the phytase was Genophos 10000G purchased from Genofocus, Inc.

Example 6. Large-Scale Production of Fructose 1,6-Bisphosphate Aldolased Enzyme Fructose 1,6-diphosphate aldolase gene was obtained in a large scale by performing PCR amplification after designing primers based on the nucleotide sequence of DNA of *Escherichia coli* strain K-12 substrain MG1655, inserting the PCR product into an RSF Duet-1 vector [Novagen] using restriction enzymes, Sal I and Not I, to construct a recombinant vector, RSF Duet-1/fructose 1,6-diphosphate aldolase (FIG. 17), followed by transforming the recombinant vector into *E. coli* BL21(DE3) by a conventional transformation method. Additionally, the recombinant *E. coli* strain was stored in liquid nitrogen prior to cultivation for a large-scale production.

For a large-scale production of fructose 1,6-diphosphate aldolase, the frozen-stored BL21(DE3) strain was inoculated into a 250-mL flask including 50 mL of LB and seed cultured in a shaking water bath maintained at 37° C. until the absorbance at 600 nm reached 2.0, and the seed-cultured culture broth was subjected to a main cultivation by adding it into a 7-L fermentor (Biotron, Korea) including 5 L of a fermentation medium (10 g/L of glycerol, 1 g/L of peptone, 30 g/L of yeast extract, 0.14 g/L of potassium diphosphate, and 1 g/L of monosodium phosphate). In particular, the large-scale production of fructose 1,6-diphosphate aldolase was induced by adding 1 mM ITPG when the absorbance at 600 nm reached 2.0. Specifically, the stirring speed at 500 rpm, aeration of 1.0 vvm, and the culture temperature at 37° C. were maintained during the above process.

Example 7. Production of Tagatose from Tagatose 6-Phosphate Using Phytase

For the production of tagatose at high concentration, 10 mM tagatose 6-phosphate converted from fructose 6-phosphate was reacted with 10 to 50 U/mL of phytase in a 50-mM pH 7.5 Trizma buffer solution (pH 5.5) at 60° C. for 60 minutes. Then, the enzyme activity was measured. The amount of tagatose production according to enzyme concentration is listed in FIG. 23.

As a result, 9 mM of tagatose was produced for 50 U/mL of cultivation time, and this corresponds to 90% of conversion yield.

Example 8. Production of Tagatose from Fructose by a Cocktail Reaction of Hexokinase, Aldolase, and Phytase Tagatose was produced from fructose by a cocktail reaction of hexokinase, aldolase, and phytase based on the Examples above. Fructose 6-phosphate was produced by reacting 5 mM fructose with an equal amount of adenosine triphosphate (ATP) and 250 U/mL of hexokinase derived from *Saccharomyces cerevisiae* in a 50-mM Trizma buffer solution (pH 7.5) at 30° C. for 60 minutes and, as a result, 100% of the 5 mM fructose was converted into 5 mM fructose 6-phosphate. As a serial reaction, when a 50-mM Trizma base buffer solution including 0.5 U/mL of fructose 1,6-bisphosphate aldolase was reacted at pH 8.5 for 30 minutes, 93% of the 5-mM fructose 6-phosphate was converted into 4.65-mM tagatose 6-phosphate. Then, when the reaction was performed in a 50-mM Trizma base buffer solution (pH 5.5) including 50 U/mL of the enzyme at 60° C. for 60 minutes, 100% of the 4.65-mM tagatose 6-phosphate was converted into 4.65-mM tagatose. Conclusively, as a result of the cocktail reaction of hexokinase, aldolase, and phytase using 5-mM fructose, 93% was successfully converted into 4.65-mM tagatose.

Example 9. Change in Activity of Gene Mutant Enzyme According to Amino Acid Substitution of Aldolase For the production of tagatose at high concentration of the disclosure, in order to increase the activity of aldolase, an amino acid substitution was caused by manipulating basic gene sequence and the change in activity of the enzyme was observed. As a result, a gene mutant enzyme, which can exhibit a fast conversion effect through a faster initial reaction speed, was successfully constructed. The gene sequences encoding the amino acids to be mutated were mutated with site-directed mutation and thereby a gene mutant enzyme was constructed. Site-directed mutation was performed using the Muta-Direct™ Site-Directed Mutagenesis Kit, and primers, in which the genes encoding 332R, 314Q, 227H, and 62S, i.e., the amino acids to be mutated, were substituted to encode glutamic acid or alanine (see sequences in Table 1), were constructed to amplify a recombinant plasmid, which was sequenced after transformation, and the strains having substituted mutant enzymes were selected via screening. The selected gene mutant enzymes were subjected to purification in the same manner as in wild-type strain according to Example 2, and reacted in a 50-mM Trizma base buffer solution (pH 8.5) including 1.0% fructose 6-phosphate and 0.04 U/mL of the enzyme for 10 minutes, for comparison of activities. In particular, the reaction was stopped by adding 0.2 M HCl, the amount of the converted tagatose 6-phosphate and the fructose 6-phosphate was analyzed, and the enzyme activity was measured by converting the activity of the wild-type enzyme into relative activity 100%. The results are illustrated in FIG. 24. As a result, the R332Q mutant showed an increase of about 140%, the Q314A showed an increase of about 250%, the H227A mutant showed an increase of about 230%, and the S62A mutant showed an increase of about 150%, relative to that of the wild-type enzyme, respectively.

TABLE 1

| Name | Nucleotide sequence 5' to 3' |
|---|---|
| S62A | GGTTATCGTTCAGTTCGCCAACGGTGGTGCTTC (SEQ ID NO: 7) |
| S62A anti | GAAGCACCACCGTTGGCGAACTGAACGATAACC (SEQ ID NO: 8) |
| H227A | GCGTCCTTCGGTAACGTAGCCGGTGTTTACAAG (SEQ ID NO: 9) |
| H227A anti | CTTGTAAACACCGGCTACGTTACCGAAGGACGC (SEQ ID NO: 10) |
| Q314A | CTTATCTGCAGGGTGCGCTGGGTAACC (SEQ ID NO: 11) |
| Q314A anti | GGTTACCCAGCGCACCCTGCAGATAAG (SEQ ID NO: 12) |
| R331Q | TACGATCCGCAGGTATGGCTGCGTGCCG (SEQ ID NO: 13) |
| R331Q anti | CGGCACGCAGCCATACCTGCGGATCGTA (SEQ ID NO: 14) |

Table 1 lists information on primers used in constructing mutants of fructose 1,6-bisphosphate aldolase.

TABLE 2

| *Escherichia coli* (strain K12) | Sal I | GTCGACTCTAAGATTTTTGATTT CGTAAAACC (SEQ ID NO: 15) |
|---|---|---|
| | Not I | GCGGCCGCTTACAGAACGTCGAT CGCGTT (SEQ ID NO: 16) |
| *Streptococcus thermophilus* | Sal I | GTCGAC GCAATCGTTTCAGCAG AAAAATTTG (SEQ ID NO: 17) |
| | Not I | GCGGCCGC TTAAGCTTTGTTTG CTGAACC (SEQ ID NO: 18) |
| *Caldicellulosiruptor saccharolyticus* | Sal I | GTCGAC CCACTTGTAACAACCA AAGAG (SEQ ID NO: 19) |
| | Not I | GCGGCCGCTTAGCCTCTGTTCTT CTTAATCTC (SEQ ID NO: 20) |
| *Kluyveromyces lactis* | Sal I | GTCGAC CCAGCTCAAGACGTAT TGACCAG (SEQ ID NO: 21) |
| | Not I | GCGGCCGC TTATTCCAAAGCAC CCTTAGTAC (SEQ ID NO: 22) |

Table 2 lists information on primers used in this disclosure for each of fructose 1,6-diphosphate aldolase gene.

The invention claimed is:

1. A mutant enzyme capable of converting fructose 6-phosphate into tagatose-6 phosphate, the mutant enzyme consisting of SEQ ID NO: 1 with one or more substitution selected from the group consisting of:
   i) a substitution of arginine residue with glutamine at a position corresponding to position 332,
   ii) a substitution of glutamine residue with alanine at a position corresponding to position 314, and
   iii) a substitution of histidine residue with alanine at a position corresponding to position 227.

2. A method of producing tagatose from fructose, the method comprising:
   reacting fructose 6-phosphate with a mutant enzyme of claim 1,
   wherein the mutant enzyme catalyzes the conversion of the fructose 6-phosphate into tagatose-6 phosphate.

* * * * *